(12) United States Patent
Descenzo et al.

(10) Patent No.: US 6,787,684 B2
(45) Date of Patent: Sep. 7, 2004

(54) **LIPOXYGENASE GENES FROM *VITIS VINIFERA***

(75) Inventors: Richard A. Descenzo, Modesto, CA (US); Nancy A. Irelan, Modesto, CA (US)

(73) Assignee: E. & J. Gallo Winery, Modesto, CA (US)

( * ) Notice: Subject to any disclaimer, the term of this patent is extended or adjusted under 35 U.S.C. 154(b) by 289 days.

(21) Appl. No.: 09/978,522

(22) Filed: Oct. 16, 2001

(65) Prior Publication Data

US 2003/0033627 A1 Feb. 13, 2003

Related U.S. Application Data

(60) Provisional application No. 60/241,220, filed on Oct. 16, 2000.

(51) Int. Cl.$^7$ ............................. A01H 1/00; A01H 5/00; C12N 15/29; C12N 15/52; C12N 15/82
(52) U.S. Cl. ...................... 800/298; 800/278; 536/23.1; 536/23.2; 536/23.6; 435/69.1; 435/70.1; 435/252.1; 435/255.1; 435/320.1; 435/419
(58) Field of Search ................................ 800/278, 298; 536/23.1, 23.2, 23.6; 435/69.1, 70.1, 252.1, 255.1, 320.1, 419

(56) References Cited

U.S. PATENT DOCUMENTS

| 4,945,050 A | 7/1990 | Sanford et al. ........... 435/172.1 |
| 5,036,006 A | 7/1991 | Sanford et al. ........... 435/170.1 |
| 5,100,792 A | 3/1992 | Sanford et al. ........... 435/172.1 |
| 5,573,926 A | 11/1996 | Gunata et al. ................ 435/74 |
| 5,705,372 A | 1/1998 | Belin et al. .................. 435/123 |
| 5,985,618 A | 11/1999 | Gunata et al. ................ 435/74 |
| 6,020,539 A | 2/2000 | Goldman et al. ........... 800/294 |
| 6,051,409 A | 4/2000 | Hansen et al. ............ 435/172.3 |
| 6,106,872 A | 8/2000 | Gunata et al. ................ 426/15 |

FOREIGN PATENT DOCUMENTS

| WO | WO 91/09955 | 7/1991 | ........... C12N/15/67 |
| WO | WO 92/20808 | 11/1992 | ........... C12N/15/85 |
| WO | WO 94/12650 | 6/1994 | ........... C12N/15/90 |
| WO | WO 02/06443 | 1/2002 | |
| WO | WO 02/06490 | 1/2002 | ........... C12N/15/53 |

OTHER PUBLICATIONS

M. Martinez–Anaya, Journal of Agricultural and Food Chemistry, 1996, vol. 44, No. 9, pp. 2469–2480.*
Angerosa et al., "Virgin Olive Oil Volatile Compounds from Lipoxygenase Pathway and Characterization of Some Italian Cultivars," *J. Agri. Food Chem.* 47:836–839 (1999).
Baribault et al., "Genetic Transformation of Grapevine Cells," *Plant Cell Reports.* 8:137–140 (1989).
Bilang et al., "The 3'–terminal Region of the Hygromycin–B–Resistance is Important for its Activity in *Escherichia coli* and *Nicotiana tabacum*," *Gene.* 100:247–250 (1991).
Bramlage et al., "Designing Ribozymes for the Inhibition of Gene Expression," *Trends in Biotech*, 16:434–438 (1998).
Cayrel et al., "Evidence for the Occurrence of Lipoxygenase Activity in grapes, (Variety Carignane)," *Amer. J. of Enology and Viticulture*, 34:77–82 (1983).
Crouzet et al., "Enzymes Occurring in the Formation of Six–Carbon Aldehydes and Alcohols in Grapes." in *Progress in Flavour Research 1984*, Proceedings of 4$^{th}$ Weurman Flavour Research Symposium (J. Adda ed.) Elsivier Science Publishers, (1985).
DeBlock et al., "Transformation of *Brassica napus* and *Brassica oleracea* Using *Agrobacterium tumefaciens* and the Expression of the *bar* and *neo* Genes in the Transgenic Plants," *Plant Physiology*, 91:694–701 (1989).
Gardner, H.W., "How the Lipoxygenase Pathway Affects the Organoleptic Properties of Fresh Fruit and Vegetables," in: Flavor Chemistry of Lipid Foods Eds. Min, D.B. and Smouse, T.H. The America Oil Chemists' Society (1989).
Gibson et al., "Ribozymes: Their Functions and Strategies for Their Use," *Mol. Biotech.*, 7:125–137 (1997).
Guerche et al., Direct Gene Transfer by Electroporation in *Brassica napus*, *Plant Science*, 52:111–116 (1987).
Hatanaka, A., "The fresh Green Odor Emitted by Plants," *Food Review International*, 12:303–350 (1996).
Horsch et al., "A Simple and General Method for Transferring Genes into Plants," *Science*, 227:1229–1231 (1985).
Howell et al., Cloned Cauliflower Mosaic Virus FNA Infects Turnips (*Brassica rapa*) *Science*, 208:1265–1267 (1980).
Klein et al., "High–velocity Microprojectiles for Delivering Nucleic Acids into Living Cells," *Nature*, 327:70–73 (1987).
Lavrosky et al., "Therapeutic Potential and Mechanism of Action of Oligonucleotides and Ribozymes," *Biochem. Mol. Med.*, 62:11–22 (1997).
Leon et al., "Lipoxygenase H1 Gene Silencing Reveals a Specific Role in Supplying Fatty Acid Hydroperoxides for Aliphatic Aldehyde Production." *J. Biol. Chem.*, 277:416–423 (2002).
Neuhause et al., "Transgenic Rapeseed Plants Obtained by the Microinjection of DNA into Microspore–derived Embyroids," *Theor. Appl. Genet.*, 75:30–36 (1987).
O'Conner et al., "Significance of Lipoxygenase in Fruits and Vegetables," *Food Enzymology*, 1:337–372 (1992).
Scheid et al., "Reversible Inactivation of a Transgene in *Arabidopsis thaliana*," *Mol. Gen. Genet.*, 228–104–112 (1991).
Waldman et al., "Stereochemical Studies of Epoxides Formed by Lipoxygenase–Catalyzed Co–oxidation of Retinol, β–Ionone, and 4–Hydroxy–β–inone," *J. of Agri. Food Chem.*, 43:626–630 (1995).

* cited by examiner

Primary Examiner—Phuong T. Bui
Assistant Examiner—Russell Kallis
(74) Attorney, Agent, or Firm—Marshall, Gerstein & Borun LLP

(57) ABSTRACT

Lipoxygenase genes from *Vitis vinifera* and polypeptides encoded thereby are provided.

15 Claims, No Drawings

LIPOXYGENASE GENES FROM *VITIS VINIFERA*

This application claims benefit of U.S. Provisional Application Ser. No. 60/241,220 filed Oct. 16, 2000.

BACKGROUND OF THE INVENTION

Lipoxygenase enzymes belong to a large, multigene-family involved in the regulation and biosynthesis of a number of biologically active compounds. They have been implicated in a number of processes including senescence, plant growth and development, mobilization of lipid reserves during seed germination disease resistance responses, vegetative storage proteins and in the production of flavor and scent compounds. The present invention is directed to the involvement of lipoxygenase enzymes in the production of flavor compounds or precursors and is particularly directed to the role of lipoxygenase enzymes in the fruit of *Vitis vinifera* (grape).

There is evidence in the literature of a connection between lipoxygenase enzyme (LOX) activity and the production of compounds associated with flavor in grape. See e.g.,Cayrel et al., *Amer. J. of Ecology and Viticulture* 34:77–82 (1983); Crouzet et al., *Progress in Flavour Research* 1984, Proceedings of the 4th Weurman Flavour Research Symposium (J. Adda ed.) Elsevier Science Publishers, (1985); Waldman and Schreier, *J. of Agri. Food Chem.*, 43:626–630 (1995); O'Conner and O'Brien, Food Enzymology 1: 337–372 (1991); Gardner, HW in: Flavor Chemistry of Lipid Foods. Eds. Min, D. B. and Smouse, T. H. The American Oil Chemists' Society (1989); Angerosa, F., et al. *J. of Agri. Food Chem.* 47: 836–839 (1999); and Hanataka, *Food Review International*, 12:303–350 (1996). Oxidation of linoleic and linolenic acids by LOX produces C9 and C13 hydroperoxides that can be further modified by other enzymes to produce C6, C9, and C12 compounds with characteristic flavors and aroma. Such C6 compounds associated with flavors and aroma include 3Z-hexenal, 3E-hexenal, 2E-hexenal, 3Z-hexenol, 3E-hexenol, 2E-hexenol, n-hexanal and n-hexenol. Such C9 compounds associated with flavors and aroma including 3Z=6Z-nonadienal, 2E-6Z-nonadienal, 3Z-6Z-nonadienol, 2E-6Z-nonadienol, 9-oxo-nonanoic acid, 3Z-nonenal, 2E-nonenal, 3Z-nonenol, 2E-nonenol and C12 flavor and aroma compounds include 12-oxo-9Z-dodecenoic acid and 12-ox-10E-dodecenoic acid.

Production of these volatiles depends on the initial fatty acid substrate, the particular LOX isozyme, and the presence of other enzymes required for formation of the different volatile compounds. In addition, free radicals released during the oxidation of fatty acids by LOX can potentially induce cooxidation of carotenoid compounds yielding a number of flavor and aroma compounds.

Lipoxygenase has been characterized in a number of species and in most cases is encoded by a member of a large gene family. In soybean, LOX is comprised of a highly conserved multigene family consisting of at least eight members. There are at least five vegetative LOX (VLX) genes involved in nitrogen storage function, that represent a major storage protein in soybean leaves. Of these, VLXD proteins increase in sink limited soybeans. VLXC+D are degraded preferentially during pod maturation, and VLXC has a dual role as a storage protein and a cytosolic enzyme. There are also three LOX genes found in the seeds, LX 1, LX2 and LX3. Analysis of cloned LOX genes reveals a highly conserved 70 kd globular domain and a 30 kd beta-barrel domain. In addition it has been observed that the N-terminus of the LOX genes is extremely divergent. (Howard Grimes presentation at the 1999 American Society of Plant Physiology titled, "Lipoxygenase Function in Assimilate Partitioning") In most plants analyzed, there exist LOX genes with similarity to both the vegetative and seed type lipoxygenases found in soybean.

Despite the identification and cloning of LOX genes in a number of plant species including soybean (*Glycine max.*), *Solanum tuberosum, Hordeum vulgare, Oryza sativa, Arabidopsis thaliana, Cucumis sativa* and *Prunus dulcis,* LOX genes have not been cloned from *Vitis vinifera* and there exists no source to obtain pure lipoxygenase from grape. Accordingly, there exists a desire in the art for pure *Vitis vinifera* LOX.

SUMMARY OF THE INVENTION

The present invention provides purified and isolated polynucleotide encoding a *Vitis vinifera* LOX polypeptide selected from the group consisting of: a) a polynucleotide comprising the sequence as set forth in SEQ ID NO: 2 or SEQ ID NO: 4, b) a DNA which hybridizes under moderately stringent conditions to the non-coding strand of the polynucleotide of (a); and c) a DNA which would hybridize to the non-coding strand of the polynucleotide of (a) but for the redundancy of the genetic code. The polynucleotide of the invention is preferably a DNA molecule and is more preferably a cDNA molecule. Alternatively, the DNA is a wholly or partially chemically synthesized DNA molecule. According to another embodiment of the invention the polynucleotide is an a) anti-sense polynucleotide which specifically hybridizes with the polynucleotide as set forth in SEQ ID NO: 2 or SEQ ID NO: 4 b) a DNA which hybridizes under moderately stringent conditions to the non-coding strand of the polynucleotide of (a); and c) a DNA which would hybridize to the non-coding strand of the polynucleotide of (a) but for the redundancy of the genetic code. The invention also provides polynucleotides where the LOX encoding sequence is operably linked to a heterologous promoter. The invention also provides expression constructs, comprising the polynucleotide of the invention, as well as host cells transformed or transfected with a polynucleotide or expression construct of the invention. The invention also provides polynucleotides of the invention operably linked to a heterologous promoter, and host cell polynucleotides operably linked to a heterologous promoter.

Host cells transformed or transfected according to the invention include those which are *Vitis vinifera* cells. The invention also provides transformed plants comprising host cells transformed or transfected with the LOX gene. Transformed plants of the invention include those wherein the expression construct comprises a polynucleotide encoding *a Vitis vinifera* LOX polypeptide operably linked to a heterologous promoter. According to one preferred embodiment the transformed plant is *Vitis vinifera*. Alternatively, transformed cells include microorganisms including those active in fermentation reactions and including those selected from the group consisting of yeast and bacteria.

The invention also provides a purified and isolated *Vitis vinifera* LOX polypeptide comprising the amino acid sequence as set forth in SEQ ID NO: 1 or SEQ ID NO: 3. Amino acid SEQ ID NOS: 1 and 3 were determined by analysis of polynucleotide SEQ ID NOS: 2 and 4, respectively, and comparison with known LOX amino acid sequences. The availability of purified LOX enzyme provided by the invention makes possible the use of the enzyme to modify food flavors by contacting a food or other comestible with a quantity of purified and isolated *Vitis vinifera* LOX polypeptide comprising the amino acid sequence as set forth in SEQ ID NO: 1 or SEQ ID NO: 3 under conditions selected to modify the flavor characteristics of the comestible. Food products, which can be treated according to the invention, include comestibles that are beverages. It is contemplated that the invention will be particularly useful in the treatment of beverages that are fermentation products and most preferably wine.

In particular, the invention provides a method for modifying the flavor of a fermented beverage, including wine, comprising the step of fermenting said beverage in the presence of a microorganism transformed or transfected with an expression construct comprising a LOX polynucleotide according to the invention. Preferred microorganisms include those selected from the group consisting of yeast and bacteria.

Cloning of the Vitis gene encoding lipoxygenase enables the heterologous production of pure lipoxyegenase enzyme in a protein expression vector. Production of sufficient quantities of enzyme allows analysis of its effect on flavor production in wine and grape juice. In addition, the cloned gene enables study of the native level of gene expression in response to environmental or viticultural influences. Further, the cloned gene can be used to produce transgenic plants to modify the level of gene expression to produce optimal levels of lipoxygenase in the grape.

DETAILED DESCRIPTION OF THE INVENTION

The present invention provides purified and isolated polypeptides and underlying polynucleotides for a novel family of lipoxygenase proteins from *Vitis vinifera*. The invention includes both naturally occurring and non-naturally occurring *Vitis vinifera* lipoxygenase polynucleotides and polypeptide products thereof. Naturally occurring *Vitis vinifera* lipoxygenase products include distinct gene and polypeptide species within the *Vitis vinifera* lipoxygenase family, including, for example, allelic variants, which are expressed within cells of grape. The invention further provides splice variants encoded by the same polynucleotide but which arise from distinct MRNA transcripts. Non-naturally occurring *Vitis vinifera* lipoxygenase products include variants of the naturally occurring products such as analogs, fragments, fusion (or chimeric) proteins, and *Vitis vinifera* lipoxygenase products having covalent modifications.

In a preferred embodiment, the invention provides polynucleotides comprising the sequences set forth in SEQ ID NO: 2 or SEQ ID NO: 4. The invention also embraces polynucleotides encoding the amino acid sequences set out in SEQ ID NO: 1 or SEQ ID NO: 3 as well as polynucleotides encoding mature polypeptides, wherein signal and/or leader sequences are removed from the polypeptides as set out in SEQ ID NO: 1 or SEQ ID NO: 3. Presently preferred polypeptides of the invention comprise the amino acid sequences set out in SEQ ID NO: 1 or SEQ ID NO: 3

The invention also provides expression constructs (or vectors) comprising polynucleotides of the invention, as well as host cells transformed, transfected, or electroporated to include a polynucleotide or expression construct of the invention. Methods to produce a polypeptide of the invention are also comprehended. The invention further provides antibodies, preferably monoclonal antibodies, which are specifically immunoreactive with a polypeptide of the invention. Also provided are cell lines, (e.g., hybridomas), that secrete the antibodies.

The present invention provides novel purified and isolated polynucleotides (e.g., DNA sequences and RNA transcripts, both sense and complementary antisense strands, including splice variants thereof) encoding the *Vitis vinifera* lipoxygenases. DNA sequences of the invention include genomic and cDNA sequences as well as wholly or partially chemically synthesized DNA sequences. Genomic DNA of the invention comprises the protein-coding region for a polypeptide of the invention and includes allelic variants of the preferred polynucleotides of the invention. Genomic DNA of the invention is distinguishable from genomic DNAs encoding polypeptides other than *Vitis vinifera* lipoxygenase in that it includes the *Vitis vinifera* lipoxygenase coding region found in *Vitis vinifera* lipoxygenase cDNA of the invention.

Genomic DNA of the invention can be transcribed into RNA, and the resulting RNA transcript may undergo one or more splicing events wherein one or more introns (i.e., non-coding regions) of the transcript are removed, or "spliced out." RNA transcripts that can be spliced by alternative mechanisms, and therefore be subjected to removal of different non-coding RNA sequences but still encode a *Vitis vinifera* lipoxygenase polypeptide, are referred to in the art as splice variants, which are embraced by the invention. Splice variants comprehended by the invention, therefore, are encoded by the same DNA sequences but arise from distinct mRNA transcripts. Allelic variants are known in the art to be modified forms of a wild type (predominant) gene sequence, the modification resulting from recombination during chromosomal segregation or exposure to conditions which give rise to genetic mutation. Allelic variants, like wild type genes, are inherently naturally occurring sequences (as opposed to non-naturally occurring variants that arise from in vitro manipulation).

The invention also comprehends cDNA that is obtained through reverse transcription of an RNA polynucleotide encoding *Vitis vinifera* lipoxygenase, followed by second strand synthesis of a complementary strand to provide a double stranded DNA.

"Chemically synthesized" as used herein and understood in the art, refers to polynucleotides produced by purely chemical, as opposed to enzymatic, methods. "Wholly" synthesized DNA sequences are therefore produced entirely by chemical means, and "partially" synthesized DNAs embrace those wherein only portions of the resulting DNA were produced by chemical means.

Preferred DNA sequences encoding *Vitis vinifera* lipoxygenase polypeptides are set out in SEQ ID NO: 2 or SEQ ID NO: 4. The worker of skill in the art will readily appreciate that preferred DNAs of the invention comprise double stranded molecules, for example, the molecule having the sequence set forth in either SEQ ID NO: 2 or SEQ ID NO: 4 along with the complementary molecule (the "non-coding strand" or "complement") having a sequence deducible from the sequence of SEQ ID NO: 2 or SEQ ID NO: 4 according to Watson-Crick base pairing rules for DNA. Also preferred are polynucleotides encoding the *Vitis vinifera* lipoxygenase polypeptides of SEQ ID NO: 1 or SEQ ID NO: 3 and polynucleotides that hybridize thereto.

The invention further embraces homologs of the *Vitis vinifera* lipoxygenase DNA. Species homologs, also known in the art as orthologs, in general, share at least 70%, at least 75%, at least 80%, at least 85%, at least 90%, at least 95%, at least 98%, or at least 99% homology with *Vitis vinifera*

DNA of the invention. Percent sequence "homology" with respect to polynucleotides of the invention is defined herein as the percentage of nucleotide bases in the candidate sequence that are identical to nucleotides in the *Vitis vinifera* lipoxygenase coding sequence after aligning the sequences and introducing gaps, if necessary, to achieve the maximum percent sequence identity.

The polynucleotide sequence information provided by the invention makes possible large-scale expression of the encoded polypeptide by techniques well known and routinely practiced in the art. Polynucleotides also permit identification and isolation of polynucleotides encoding related *Vitis vinifera* lipoxygenase polypeptides by well known techniques including Southern and/or Northern hybridization, and polymerase chain reaction (PCR), ligase chain reaction, as well as other amplification techniques. Examples of related polynucleotides include genomic sequences, including allelic variants, as well as polynucleotides encoding polypeptides homologous to *Vitis vinifera* lipoxygenases and structurally related polypeptides sharing one or more biological, immunological, and/or physical properties of *Vitis vinifera* lipoxygenase.

The disclosure of polynucleotides encoding *Vitis vinifera* lipoxygenase polypeptides makes readily available to the worker of ordinary skill in the art every possible fragment of those polynucleotides. The invention therefore provides fragments of *Vitis vinifera* lipoxygenase coding polynucleotides. Such fragments comprise at least 10 to 20, and preferably at least 15, consecutive nucleotides of the polynucleotide. The invention comprehends, however, fragments of various lengths. Preferably, fragment polynucleotides of the invention comprise sequences unique to the *Vitis vinifera* lipoxygenase coding polynucleotide sequence, and therefore hybridize under highly stringent or moderately stringent conditions only (i.e., "specifically") to polynucleotides encoding *Vitis vinifera* lipoxygenase, or *Vitis vinifera* lipoxygenase fragments thereof containing the unique sequence. Polynucleotide fragments of genomic sequences of the invention comprise not only sequences unique to the coding region, but also include fragments of the full length sequence derived from introns, regulatory regions, and/or other non-translated sequences. Sequences unique to polynucleotides of the invention are recognizable through sequence comparison to other known polynucleotides, and can be identified through use of alignment programs routinely utilized in the art, e.g., those made available in public sequence databases.

The invention also provides fragment polynucleotides that are conserved in one or more polynucleotides encoding members of the *Vitis vinifera* lipoxygenase family of polypeptides. Such fragments include sequences characteristic of the family of *Vitis vinifera* lipoxygenase polynucleotides, and are referred to as "signature sequences." The conserved signature sequences are readily discernable following simple sequence comparison of polynucleotides encoding members of the *Vitis vinifera* lipoxygenase family. Fragments of the invention can be labeled in a manner that permits their detection, including radioactive and non-radioactive labeling.

Fragment polynucleotides are particularly useful as probes for detection of full length or other fragments of *Vitis vinifera* lipoxygenase coding polynucleotides. One or more fragment polynucleotides can be included in kits that are used to detect the presence of a polynucleotide encoding *Vitis vinifera* lipoxygenase, or used to detect variations in a polynucleotide sequence encoding *Vitis vinifera* lipoxygenase.

The invention also embraces DNA sequences encoding *Vitis vinifera* lipoxygenase species which hybridize under moderately or highly stringent conditions to the non-coding strand, or complement, of the polynucleotide in SEQ ID NO: 1 or SEQ ID NO: 3 encoding *Vitis vinifera* lipoxygenase polypeptides which would hybridize thereto but for the redundancy of the genetic code are further comprehended by the invention. The invention also provides polynucleotides that hybridize under moderate to high stringency conditions to polynucleotides encoding the *Vitis vinifera* lipoxygenase polypeptides in SEQ ID NO: 1 or SEQ ID NO: 3. Exemplary highly stringent conditions include hybridization at 45° C. in 5×SSPE and 45% formamide, and a final wash at 65° C. in 0. 1×SSC. Exemplary moderately stringent conditions include a final wash at 55° C. in 1×SSC. It is understood in the art that conditions of equivalent stringency can be achieved through variation of temperature and buffer, or salt concentration as described Ausubel, et al. (Eds.), *Protocols in Molecular Biology*, John Wiley & Sons (1994), pp. 6.0.3 to 6.4.10. Modifications in hybridization conditions can be empirically determined or precisely calculated based on the length and the percentage of guanosine/cytosine (GC) base pairing of the probe. The hybridization conditions can be calculated as described in Sambrook, et al., (Eds.), *Molecular Cloning: A Laboratory Manual*, Cold Spring Harbor Laboratory Press: Cold Spring Harbor, N.Y. (1989), pp. 9.47 to 9.51.

Autonomously replicating recombinant expression constructs such as plasmid and viral DNA vectors incorporating *Vitis vinifera* lipoxygenase coding sequences are also provided. Expression constructs wherein *Vitis vinifera* lipoxygenase-encoding polynucleotides are operably linked to an endogenous or exogenous expression control DNA sequence and a transcription terminator are also provided. Expression control DNA sequences include promoters, enhancers, and operators, and are generally selected based on the expression systems in which the expression construct is to be utilized. Preferred promoter and enhancer sequences are generally selected for the ability to increase gene expression. More specifically, tissue-specific promoter sequences such as those which direct expression of the LOX DNA in the Vitus vinifera fruit (the grape) may be particularly preferred for use with the invention. Operator sequences are generally selected for the ability to regulate gene expression. Expression constructs of the invention may also include sequences encoding one or more selectable markers that permit identification of host cells bearing the construct. Expression constructs may also include sequences that facilitate, and preferably promote, homologous recombination in a host cell. Preferred constructs of the invention also include sequences necessary for replication in a host cell. Expression constructs are preferably utilized for production of an encoded *Vitis vinifera* lipoxygenase protein, but may also be utilized to amplify the construct itself.

According to another aspect of the invention, host cells are provided, including prokaryotic and eukaryotic, including plant cells, comprising a polynucleotide of the invention in a manner that permits expression of the encoded *Vitis vinifera* lipoxygenase polypeptide. Suitable host cells for transformation with the *Vitis vinifera* LOX genes of the invention include plants, including but not limited to, *Vitis vinifera* as well as bacteria, yeasts and other fungi which can be used in wine fermentation processes. Polynucleotides of the invention may be introduced into the host cell as part of a circular plasmid, or as linear DNA comprising an isolated protein coding region or a viral vector. Methods for introducing DNA into the host cell that are well known and routinely practiced in the art include transformation, transfection, electroporation, nuclear injection, transformation by Agrobacterium infection, or by transformation of pollen or fusion with carriers such as liposomes, micelles, ghost cells, and protoplasts. Expression systems of the invention include systems such as bacterial, yeast, fungal, plant, insect, invertebrate, and mammalian cells systems. Host cells of the invention are a valuable source of immunogen for development of antibodies specifically immunoreactive with *Vitis vinifera* lipoxygenase.

Various transformation methods useful for practice of the invention include those disclosed in U.S. Pat. No. 6,051,409, which are hereby incorporated by reference. Such methods used for transfer of DNA into plant cells include, for example, direct DNA uptake, Agrobacterium tumefaciens infection, liposomes, electroporation, micro-injection and microprojectiles. See for example, Bilang, et al., *Gene* 100: 247–250 (1991); Scheid et al., *Mol. Gen. Genet.* 228: 104–112 (1991); Guerche et al., *Plant Science* 52:111–116 (1987); Neuhause et al., *Theor. Appi. Genet.* 75: 30–36 (1987); Klein et al., *Nature* 327:70–73 (1987); Howell et al., *Science* 208: 1265 (1980); Horsch et al., *Science* 227:122901231 (1985); DeBlock et al., *Plant Physiology* 91:694–701 (1989); *Methods for Plant Molecular Biology* (Weissbach and Weissbach, eds.) Academic Press Inc. (1988); and *Methods in Plant Molecular Biology* (Schuler and Zielinski eds.) Academic Press Inc. (1989). See also Goldman et al., U.S. Pat. No. 6,020,539 and Sanford U.S. Pat. Nos. 4,945,050; 5,036,006 and 5,100,792 the disclosures of which are incorporated by reference. See also Baribault et al., Plant Cell Reports 8:137 (1989) which discloses the transformation of *Vitus vinifera* with foreign DNA.

Host cells of the invention are also useful in methods for large scale production of *Vitis vinifera* lipoxygenase polypeptides wherein the cells are grown in a suitable culture medium and the desired polypeptide products are isolated from the cells or from the medium in which the cells are grown by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC and the like. Still other methods of purification include those wherein the desired protein is expressed and purified as a fusion protein having a specific tag, label, or chelating moiety that is recognized by a specific binding partner or agent. The purified protein can be cleaved to yield the desired protein, or be left as an intact fusion protein. Cleavage of the fusion component may produce a form of the desired protein having additional amino acid residues, resulting from the cleavage process.

Knowledge of *Vitis vinifera* lipoxygenase coding DNA sequences allows for modification of cells to permit, increase or decrease, expression of endogenous *Vitis vinifera* lipoxygenase. Such knowledge also permits modification of timing and tissue specificity of LOX expression. Cells can be modified (e.g., by homologous recombination) to provide increased *Vitis vinifera* lipoxygenase expression by replacing, in whole or in part, the naturally occurring *Vitis vinifera* lipoxygenase promoter with all or part of a heterologous promoter so that the cells express *Vitis vinifera* lipoxygenase at higher levels. The heterologous promoter is inserted in such a manner that it is operably linked to *Vitis vinifera* lipoxygenase-encoding sequences. See, for example, PCT International Publication No. WO 94/12650, PCT International Publication No. WO 92/20808, and PCT International Publication No. WO 91/09955. It is also contemplated that, in addition to heterologous promoter DNA, amplifiable marker DNA (e.g., ada, dhfr, and the multifunctional CAD gene which encodes carbamyl phosphate synthase, aspartate transcarbamylase, and dihydroorotase) and/or intron DNA may be inserted along with the heterologous promoter DNA. If linked to the *Vitis vinifera* lipoxygenase coding sequence, amplification of the marker DNA by standard selection methods results in co-amplification of the *Vitis vinifera* lipoxygenase coding sequences in the cells.

The DNA sequence information provided by the present invention also makes possible the development through, e.g. homologous recombination or "knock-out" strategies [Capecchi, *Science* 244:1288–1292 (1989)], of grapes that fail to express functional lipoxygenase or that express a variant of *Vitis vinifera* lipoxygenase. Such plants are useful as models for studying the in vivo activities of *Vitis vinifera* lipoxygenase and modulators of *Vitis vinifera* lipoxygenase.

The invention also provides purified and isolated *Vitis vinifera* lipoxygenase polypeptides encoded by a polynucleotide of the invention. Presently preferred are *Vitis vinifera* lipoxygenase polypeptides comprising the amino acid sequence set out in SEQ ID NO: 1 or SEQ ID NO: 3, as well as mature *Vitis vinifera* lipoxygenase polypeptides wherein signal and/or leader sequences are removed from the polypeptides of SEQ ID NO: 1 or SEQ ID NO: 3. The invention also embraces *Vitis vinifera* lipoxygenase polypeptides encoded by a DNA selected from the group consisting of: a) the DNA sequence set out in SEQ ID NO: 2 or SEQ ID NO: 4; b) a DNA molecule which hybridizes under high stringent conditions to the noncoding strand of the protein coding portion of (a); and c) a DNA molecule that would hybridize to the DNA of (a) but for the degeneracy of the genetic code. The invention further provides *Vitis vinifera* lipoxygenase polypeptides encoded by a polynucleotide selected from the group consisting of: a) the polynucleotide set out in SEQ ID NO: 2 or SEQ ID NO: 4; b) a polynucleotide encoding a polypeptide set out in SEQ ID NO: 1 or SEQ ID NO: 3; and c) a polynucleotide that hybridizes to the polynucleotide of (a) or (b) under highly or moderately stringent conditions.

The invention also embraces variant (or analog) *Vitis vinifera* lipoxygenase polypeptides. It is contemplated that such variant *Vitis vinifera* LOX polypeptides will be characterized by variant and potentially improved lipoxygenase activities and will be useful in modifying the sensory character of food and beverage products with which they are reacted. The invention further provides methods by which the affects of *Vitis vinifera* LOX polypeptides on the production of flavor compounds and precursors is determined. Specifically, a method is provided by which the effects of oxidation of linoleic, linolenic and other organic acids by the *Vitis vinifera* lipoxygenase polypeptides of the invention and their variants to produce C9 and C13 hydroperoxides and other products are determined to evaluate the effects on enzymatic activity resulting from structural variation of the *Vitis vinifera* lipoxygenase polypeptides. The invention also provides for methods in which the effects of *Vitis vinifera* lipoxygenase polypeptide structural variants on the sensory character of food and beverage products are determined.

Variants according to the invention include insertion variants wherein one or more amino acid residues supplement a *Vitis vinifera* lipoxygenase amino acid sequence. Insertions may be located at either or both termini of the protein, or may be positioned within internal regions of the *Vitis vinifera* lipoxygenase amino acid sequence. Insertional variants with additional residues at either or both termini can include for example, fusion proteins and proteins including amino acid tags or labels.

In another aspect, the invention provides deletion variants wherein one or more amino acid residues in a *Vitis vinifera* lipoxygenase polypeptide are removed. Deletions can be effected at one or both termini of the *Vitis vinifera* lipoxygenase polypeptide, or with removal of one or more residues within the *Vitis vinifera* lipoxygenase amino acid sequence. Deletion variants, therefore, include all fragments and truncations of a *Vitis vinifera* lipoxygenase polypeptide.

In still another aspect, the invention provides substitution variants of *Vitis vinifera* lipoxygenase polypeptides. Substitution variants include those polypeptides wherein one or more amino acid residues of a *Vitis vinifera* lipoxygenase polypeptide are removed and replaced with alternative residues. In one aspect, the substitutions are conservative in nature, however the invention embraces substitutions that are also non-conservative. Conservative substitutions for this purpose may be defined as set out in Tables 1, 2 or 3 below.

The invention also provides derivatives of *Vitis vinifera* lipoxygenase polypeptides. Derivatives include *Vitis vinifera* lipoxygenase polypeptides bearing modifications other than insertion, deletion, or substitution of amino acid residues. Preferably, the modifications are covalent in nature, and include, for example, chemical bonding with polymers, lipids, non-naturally occurring amino acids, other organic and inorganic moieties. Derivatives of the invention may be prepared to increase circulating half-life of a *Vitis vinifera* lipoxygenase polypeptide, or may be designed to improve targeting capacity for the polypeptide to desired cells, tissues, or organs.

The invention also embraces polypeptides have at least 99%, at least 95%, at least 90%, at least 85%, at least 80%, at least 75% or at least 70% identity and/or homology to the preferred polypeptide of the invention. Percent amino acid sequence "identity" with respect to the preferred polypeptide of the invention is defined herein as the percentage of amino acid residues in the candidate sequence that are identical with the residues in the *Vitis vinifera* lipoxygenase sequence after aligning both sequences and introducing gaps, if necessary, to achieve the maximum percent sequence identity, and not considering any conservative substitutions as part of the sequence identity. Percent sequence "homology" with respect to the preferred polypeptide of the invention is defined herein as the percentage of amino acid residues in the candidate sequence that are identical with the residues in the *Vitis vinifera* lipoxygenase sequence after aligning the sequences and introducing gaps, if necessary, to achieve the maximum percent sequence identity, and also considering any conservative substitutions as part of the sequence identity.

In one aspect, percent homology is calculated as the percentage of amino acid residues in the smaller of two sequences which align with identical amino acid residue in the sequence being compared, when four gaps in a length of 100 amino acids may be introduced to maximize alignment [Dayhoff, in *Altas of Protein Sequence and Structure*, Vol. 5, p. 124, National Biochemical Research Foundation, Washington, D.C. (1972), incorporated herein by reference].

Polypeptides of the invention may be isolated from natural cell sources or may be chemically synthesized, but are preferably produced by recombinant procedures involving host cells of the invention.

Insertion variants include *Vitis vinifera* lipoxygenase polypeptides wherein one or more amino acid residues are added to a *Vitis vinifera* lipoxygenase acid sequence, or fragment thereof. Variant products of the invention also include mature *Vitis vinifera* lipoxygenase products, i.e., *Vitis vinifera* lipoxygenase products wherein leader or signal sequences are removed, with additional amino terminal residues. The additional amino terminal residues may be derived from another protein, or may include one or more residues that are not identifiable as being derived from a specific proteins. *Vitis vinifera* lipoxygenase products with an additional methionine residue at position −1 (Met-1-lipoxygenase) are contemplated, as are *Vitis vinifera* lipoxygenase products with additional methionine and lysine residues at positions −2 and −1 (Met-2-Lys-1-lipoxygenase). Variants of *Vitis vinifera* lipoxygenase with multiple, additional Met, Met-Lys, Lys residues are particularly useful for enhanced recombinant protein production in bacterial host cell.

The invention also embraces *Vitis vinifera* lipoxygenase variants having additional amino acid residues which result from use of specific expression systems. For example, use of commercially available vectors that express a desired polypeptide as part of glutathione-S-transferase (GST) fusion product provides the desired polypeptide having an additional glycine residue at position −1 after cleavage of the GST component from the desired polypeptide. Variants which result from expression in other vector systems are also contemplated.

Insertional variants also include fusion proteins wherein the amino and/or carboxy termini of the *Vitis vinifera* lipoxygenase polypeptide is fused to another polypeptide. Examples of such fusion proteins are those in which transit peptides, marker proteins (e.g., fluorescent) and proteins or polypeptide that facilitate isolation, transport or purification of the desired *Vitis vinifera* lipoxygenase polypeptide, e.g. FLAG® tags or polyhistidine sequences.

Deletion variants include *Vitis vinifera* lipoxygenase polypeptides wherein one or more amino acid residues are deleted from the *Vitis vinifera* lipoxygenase amino acid sequence. Deletion variants of the invention embrace polypeptide fragments of the sequence set out in SEQ ID NO: 1 or SEQ ID NO: 3 wherein the fragments maintain biological or immunological properties of a *Vitis vinifera* lipoxygenase polypeptide. Fragments comprising at least 5, 10, 15, 20, 25, 30, 35, or 40 consecutive amino acids of SEQ ID NO: 1 or SEQ ID NO: 3 are comprehended by the invention. Preferred polypeptide fragments display antigenic properties unique to or specific for the *Vitis vinifera* lipoxygenase family of polypeptides. Fragments of the invention having the desired biological and immunological properties can be prepared by any of the methods well known and routinely practiced in the art.

Substitution variants of the invention include *Vitis vinifera* lipoxygenase polypeptides, or fragments thereof, wherein one or more amino acid residues in the *Vitis vinifera* lipoxygenase amino acid sequence are deleted and replaced with another amino acid residue. Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table 1 (from WO 97/09433, page 10, published Mar. 13, 1997 (PCT/GB96/02197, filed Sep. 6, 1996), immediately below.

TABLE 1

Conservative Substitutions I

| SIDE CHAIN CHARACTERISTIC | | AMINO ACID |
|---|---|---|
| Aliphatic | Non-polar | G A P |
| | | I L V |
| | Polar - uncharged | C S T M |
| | | N Q |
| | Polar - charged | D E |
| | | K R |
| Aromatic | | H F W Y |
| Other | | N Q D E |

Alternatively, conservative amino acids can be grouped as described in Lehninger, [*Biochemistry*, Second Edition; Worth Publishers, Inc. NY:N.Y. (1975), pp.71–77] as set out in Table 2, immediately below.

TABLE 2

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still an another alternative, exemplary conservative substitutions are set out in Table 3, below.

TABLE 3

Conservative Substitutions III

| Original Residue | Exemplary Substitution |
|---|---|
| Ala (A) | Val, Leu Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

The invention also provides methods for modifying the flavor of foods and beverages (comestibles) by using the purified *Vitis vinifera* LOX polypeptides of the invention to oxidize fatty acid substrates such as linoleic and linolenic acids to produce C9 and C13 hydroperoxides. The resulting hydroperoxides are then converted by other enzymes to produce C6, C9 and C12 compounds with characteristic flavors and aromas including 3Z-hexenal, 3E-hexenal, 2E-hexenal, 3Z-hexenol, 3E-hexenol, 2E-hexenol, n-hexanal, n-hexenol, 3Z=6Z-nonadienal, 2E-6Z-nonadienal, 3Z-6Z-nonadienol, 2E-6Z-nonadienol, 9-oxo-nonanoic acid, 3Z-nonenal, 2E-nonenal, 3Z-nonenol, 2E-nonenol, 12-oxo-9Z-dodecenoic acid and 12-ox-10E-dodecenoic acid. The use of the purified *Vitis vinifera* LOX polypeptide of the invention and of pure variants is contemplated to provide the food scientist with the ability to more specifically control the oxidation of linoleic and linolenic acids and thereby to control the quantity and identity of flavor compounds present in particular food and beverage products. Specifically, the invention provides for methods in which the flavor of a comestible product is modified by contacting the comestible with a quantity of purified and isolated *Vitis vinifera* LOX polypeptide under conditions selected to modify the flavor characteristics of the comestible. In particular, the purified LOX enzyme is expected to catalyze the conversion of fatty acid substrates such as linoleic and linolenic acids to produce products wherein hydroperoxide and other products having characteristic flavors. Moreover, the products of the LOX enzyme activity may be further modified by other reactions to produce other flavor compounds. Preferred comestibles for practice of this aspect of the invention are beverages, with fermented beverages being particularly preferred. Beverages comprising or produced from fruit juices including grape juice are a particularly preferred substrate for practice of this aspect of the invention. According to one particular aspect of the invention the fermentation products of grape and other juices (wine) may have their flavor characteristics modified by contacting with a purified and isolated *Vitis vinifera* LOX polypeptide according to the invention.

While one aspect of the invention contemplates the direct admixture of the purified *Vitis vinifera* LOX polypeptides of the invention with comestibles, an alternative aspect of the invention recognizes that the flavors of food and beverages can be modified by fermentation in the presence of a microorganism transformed or transfected with polynucleotides expressing the purified *Vitis vinifera* LOX polypeptides of the invention. Such methods are particularly useful in the fermentation of alcoholic beverages such as wine where conversion of the fatty acid substrates present in grape juice (must) is promoted by the LOX enzyme activity, but are also contemplated to be useful in other food producing processes such as those for the production of cheese, yogurt, pickles and the like which are dependent upon the action of microorganisms to provide acceptable flavor and texture to the resulting food product. Preferred microorganisms for practice of this aspect of the invention include those selected from the group consisting of yeast and bacteria. These microorganisms can be genetically transformed by techniques well known to those of skill in the art.

Also contemplated by the invention are methods in which pure flavoring compounds are produced under controlled conditions in vitro rather than in the milieu of a complex food product. According to such methods, selected substrates can be converted using the LOX activity of the purified *Vitis vinifera* LOX polypeptides of the invention to produce purified C9 and C13 hydroperoxides or other reaction products. Those reaction products can then be isolated and used as food ingredients or alternatively, can be converted by other reaction methods to yield purified flavoring compounds for addition to food and beverage products.

As discussed above, one way in which the invention is practiced to modify the flavor of foods involves genetic modification of the basic agricultural product from which the food is produced. Thus, expression of the purified *Vitis vinifera* LOX polypeptides of the invention at levels other than those naturally present in the fruit of the grape plant will modify the flavor characteristic of the resulting grapes by conversion of the fatty acid substrates within the grape.

The present invention also provides antibodies (e.g., monoclonal and polyclonal antibodies, single chain antibodies, chimeric antibodies, bifunctional/bispecific antibodies, and CDR-grafted antibodies, including compounds which include CDR sequences which specifically recognize a polypeptide of the invention) and other binding proteins specific for *Vitis vinifera* lipoxygenase products or fragments thereof. Antibody fragments, including Fab, Fab', $F(ab')_2$, and $F_v$, are also provided by the invention. The term "specific for" indicates that the variable regions of the antibodies of the invention recognize and bind *Vitis vinifera* lipoxygenase polypeptides exclusively (i.e., able to distinguish single *Vitis vinifera* lipoxygenase polypeptides from the family of *Vitis vinifera* lipoxygenase polypeptides despite sequence identity, homology, or similarity found in the family of polypeptides), but may also interact with other proteins (for example, S. aureus protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (Eds), *Antibodies: A Laboratory Manual;* Cold Spring Harbor Laboratory; Cold Spring Harbor, N.Y. (1988), Chapter 6. Antibodies that recognize and bind fragments of the *Vitis vinifera* lipoxygenase polypeptides of the invention are also contemplated, provided that the antibodies are first and foremost specific for, as defined above, *Vitis vinifera* lipoxygenase polypeptides. As with antibodies that are specific for full length *Vitis vinifera* lipoxygenase polypeptides, antibodies of the invention that recognize *Vitis vinifera* lipoxygenase fragments are those which can distinguish single and distinct *Vitis vinifera* lipoxygenase polypeptides from the family of *Vitis vinifera* lipoxygenase polypeptides despite inherent sequence identity, homology, or similarity found in the family of proteins. Antibodies of the invention can be produced using any method well known and routinely practiced in the art.

Antibodies of the invention are useful for diagnostic purposes to detect or quantitate *Vitis vinifera* lipoxygenase present in fermentation media as well as in agricultural products such as grapes, as well as purification of *Vitis vinifera* lipoxygenase. Antibodies are particularly useful for detecting and/or quantitating *Vitis vinifera* lipoxygenase expression in cells, tissues, organs and lysates and extracts thereof, as well as fluids, including grape juice, wine must and wine (collectively "wine"). Kits comprising an antibody of the invention for any of the purposes described herein are also comprehended. In general, a kit of the invention, with or without a container, also includes a control antigen for which the antibody is immunospecific.

The DNA and amino acid sequence information provided by the present invention also makes possible the systematic analysis of the structure and function of *Vitis vinifera* lipoxygenases DNA and amino acid sequence information for *Vitis vinifera* lipoxygenase also permits identification of binding partner compounds with which a *Vitis vinifera* lipoxygenase polypeptide or polynucleotide will interact. Agents that modulate (i.e., increase, decrease, or block) *Vitis vinifera* lipoxygenase activity or expression may be identified by incubating a putative modulator with a *Vitis vinifera* lipoxygenase polypeptide or polynucleotide and determining the effect of the putative modulator on *Vitis vinifera* lipoxygenase activity or expression. The selectivity of a compound that modulates the activity of the *Vitis vinifera* lipoxygenase can be evaluated by comparing its binding activity to one particular *Vitis vinifera* lipoxygenase to its activity to other *Vitis vinifera* lipoxygenase polypeptides. Cell based methods, such as di-hybrid assays to identify DNAs encoding binding compounds and split hybrid assays to identify inhibitors of *Vitis vinifera* lipoxygenase polypeptide interaction with a known binding polypeptide, as well as in vitro methods, including assays wherein a *Vitis vinifera* lipoxygenase polypeptide, *Vitis vinifera* lipoxygenase polynucleotide, or a binding partner are immobilized, and solution assays are contemplated by the invention.

Selective modulators may include, for example, antibodies and other proteins or peptides which specifically bind to a *Vitis vinifera* lipoxygenase polypeptide or a *Vitis vinifera* lipoxygenase-encoding nucleic acid, oligonucleotides which specifically bind to a *Vitis vinifera* lipoxygenase polypeptide or a *Vitis vinifera* lipoxygenase gene sequence, and other non-peptide compounds (e.g., isolated or synthetic organic and inorganic molecules) which specifically react with a *Vitis vinifera* lipoxygenase polypeptide or its underlying nucleic acid. Mutant *Vitis vinifera* lipoxygenase polypeptides which affect the enzymatic activity or cellular localization of the wild-type *Vitis vinifera* lipoxygenase polypeptides are also contemplated by the invention. Presently preferred targets for the development of selective modulators include, for example: (1) regions of the *Vitis vinifera* lipoxygenase polypeptide which contact other proteins, (2) regions that localize the *Vitis vinifera* lipoxygenase polypeptide within a cell, (3) regions of the *Vitis vinifera* lipoxygenase polypeptide which bind substrate, (4) allosteric regulatory binding site(s) of the *Vitis vinifera* lipoxygenase polypeptide, (5) site(s) of the *Vitis vinifera* lipoxygenase polypeptide wherein covalent modification regulates biological activity and (6) regions of the *Vitis vinifera* lipoxygenase polypeptide which are or could be altered to be involved in multimerization of *Vitis vinifera* lipoxygenase subunits. Still other selective modulators include those that recognize specific *Vitis vinifera* lipoxygenase encoding and regulatory polynucleotide sequences. Modulators of *Vitis vinifera* lipoxygenase activity may be therapeutically useful in treatment of a wide range of diseases and physiological conditions in which *Vitis vinifera* lipoxygenase activity is known or suspected to be involved.

The invention also provides methods to modulate binding between *Vitis vinifera* lipoxygenase and a binding partner thereof, said method comprising the step of contacting *Vitis vinifera* lipoxygenase or the binding partner with a modulator of binding between *Vitis vinifera* lipoxygenase and the binding partner. Still other selective modulators include those that recognize specific *Vitis vinifera* lipoxygenase encoding and regulatory polynucleotide sequences. Modulators of *Vitis vinifera* lipoxygenase activity may be therapeutically useful in treatment of a wide range of diseases and physiological conditions in which *Vitis vinifera* lipoxygenase activity is known or suspected to be involved.

The invention also provides methods to modulate binding between *Vitis vinifera* lipoxygenase and a binding partner thereof, said method comprising the step of contacting *Vitis vinifera* lipoxygenase or the binding partner with a modulator of binding between *Vitis vinifera* lipoxygenase and the binding partner. The methods may result in increased binding when the modulator is an enhancer of binding, or may result in decreased binding when the modulator is an inhibitor of binding.

Also made available by the invention are antisense polynucleotides which recognize and hybridize to polynucleotides encoding *Vitis vinifera* lipoxygenase. Full length and fragment antisense polynucleotides are provided. The worker of ordinary skill will appreciate that fragment antisense molecules of the invention include (i) those which specifically recognize and hybridize to *Vitis vinifera* lipoxygenase RNA (as determined by sequence comparison of DNA encoding *Vitis vinifera* lipoxygenase to DNA encoding other known molecules) as well as (ii) those which recognize and hybridize to RNA encoding variants of the *Vitis vinifera* lipoxygenase family of proteins. Antisense polynucleotides that hybridize to RNA encoding other members of the lipoxygenase family of proteins are also identifiable through sequence comparison to identify characteristic, or signature, sequences for the family of molecules. Antisense polynucleotides are particularly relevant to regulating expression of *Vitis vinifera* lipoxygenase by those cells expressing *Vitis vinifera* lipoxygenase MRNA.

Antisense nucleic acids (preferably 10 to 20 base pair oligonucleotides) capable of specifically binding to *Vitis vinifera* lipoxygenase expression-control-sequences or *Vitis vinifera* lipoxygenase RNA are introduced into cells (e.g., by a viral vector or colloidal dispersion system such as a liposome). The antisense nucleic acid binds to the *Vitis vinifera* lipoxygenase target nucleotide sequence in the cell and prevents transcription or translation of the target sequence. Phosphorothioate and methylphosphonate antisense oligonucleotides are specifically contemplated for therapeutic use by the invention. The antisense oligonucleotides may be further modified by poly-L-lysine, transferrin polylysine, or cholesterol moieties at their 5¢ ends.

The invention further contemplates methods to modulate *Vitis vinifera* lipoxygenase expression through use of ribozymes. For a review, see Gibson and Shillitoe, *Mol. Biotech.* 7:125–137 (1997). Ribozyme technology can be utilized to inhibit translation of *Vitis vinifera* lipoxygenase mRNA in a sequence specific manner through (i) the hybridization of a complementary RNA to a target mRNA and (ii) cleavage of the hybridized mRNA through nuclease activity inherent to the complementary strand. Ribozymes can be identified by empirical methods but more preferably are specifically designed based on accessible sites on the target mRNA (Bramlage, et al., *Trends in Biotech* 16:434–438 (1998). Delivery of ribozymes to target cells can be accomplished using either exogenous or endogenous delivery techniques well known and routinely practiced in the art. Exogenous delivery methods can include use of targeting liposomes or direct local injection. Endogenous methods include use of viral vectors and non-viral plasmids.

Ribozymes can specifically modulate expression of *Vitis vinifera* lipoxygenase when designed to be complementary to regions unique to a polynucleotide encoding *Vitis vinifera* lipoxygenase. "Specifically modulate" therefore is intended to mean that ribozymes of the invention recognize only a polynucleotide encoding *Vitis vinifera* lipoxygenase. Similarly, ribozymes can be designed to modulate expression of all or some of the *Vitis vinifera* lipoxygenase family of proteins. Ribozymes of this type are designed to recognize polynucleotide sequences conserved in all or some of the polynucleotides which encode the family of proteins.

The invention further embraces methods to modulate transcription of *Vitis vinifera* lipoxygenase through use of oligonucleotide-directed triplet helix formation. For a review, see Lavrovsky, et al., *Biochem. Mol. Med.* 62:11–22 (1997). Triplet helix formation is accomplished using sequence specific oligonucleotides which hybridize to double stranded DNA in the major groove as defined in the Watson-Crick model. Hybridization of a sequence specific oligonucleotide can thereafter modulate activity of DNA-binding proteins, including, for example, transcription factors and polymerases. Preferred target sequences for hybridization include promoter and enhancer regions to permit transcriptional regulation of *Vitis vinifera* lipoxygenase expression.

Oligonucleotides which are capable of triplet helix formation are also useful for site-specific covalent modification of target DNA sequences. Oligonucleotides useful for covalent modification are coupled to various DNA damaging agents as described in Lavrovsky, et al. [supra].

The present invention is illustrated by the following examples. Example 1 describes isolation of DNA primer sequences coding for lipoxygenase from *Vitis vinifera*. Example 2 relates to isolation of a DNA sequence coding for lipoxygenase from a *Vitis vinifera* cv. Cabernet Sauvignon stem cDNA library. Example 3 relates to the generation of a complette LOX DNA genomic sequences derived from a *Vitis Vinifera* Cabernet Sauvignon genomic library constructed using a Bacterial Artificial Chromosome vector.

EXAMPLE 1

According to this example, the candidate gene approach was used to isolate the DNA sequence coding for lipoxygenase from *Vitis vinifera*. This approach took advantage of the highly conserved nature of catalytic sites in lipoxygenase genes that have been cloned and sequenced from other plants. (See Table 4 below)

TABLE 4

| Gene Name | Plant Source | Genbank Accession |
| --- | --- | --- |
| Lipoxygenase-7 | *Glycine Max* | U36191 |
| Lipoxygenase-2 | *Glycine Max* | J03211 |
| Lipoxygenase-5 | *Solanum tuberosoum* | AF039651 |
| Lipoxygenase | *Solanum tuberosoum* | U24232 |
| Lipoxygenase | *Hordeum vulgare* | L37358 |
| Lipoxygenase | *Hordeum vulgare* | L37359 |
| Lipoxygenase-2 | *Glycine max* | D13949 |
| Lipoxygenase | *Glycine max* | X56139 |
| Lipoxygenase-2 | *Oryza sativa* | S37328 |
| Lipoxygenase | *Arabidopsis thaliana* | L04637 |
| Lipoxygenase | *Glycine max* | U26457 |
| Lipoxygenase-3 | *Glycine max* | U50081 |
| Lipoxygenase-2 | *Arabidopsis thaliana* | L23968 |
| Lipoxygenase-1 | *Hordeum vulgare* | L35931 |
| Lipoxygenase-L-5 | *Glycine max* | U50075 |
| Lipoxygenase | *Cucumis sativus* | U36339 |

The accessions of Table 4 were used to design the first degenerate primers. Specifically, the sequences were aligned with MegAlign4.0 from DNASTAR Inc. Sequences were aligned using the Clustal method with the PAM250 (Percent Accepted Mutation) residue weight table. A PAM(x) substitution matrix is a look-up table in which scores for each amino acid substitution have been calculated based on the frequency of that substitution in closely related proteins that have experienced a certain amount (x) of evolutionary divergence. The PAM 250 Matrix allows for a medium to strong match over a medium length of sequence, and is the default value for this program.

Degenerate primers were designed based on four highly conserved regions. Region 1 consists of amino acid residues 274–283, region 2 from residues 423–429, region 3 from residues 588–595, and region 4 from residues 780–788 wherein the numbering is based on the consensus sequence derived from the 16 analyzed sequences. The following degenerate primers were synthesized using an ABI 394 DNA synthesizer (PE Biosystems, Foster City, Calif. 94494) and all chemicals and methods used were according to the manufacturer's instructions. The primers are shown in Table 5 below.

TABLE 5

| Printer Name | Starting Nucleotide | Primer Length | Sequence 5'-3' |
| --- | --- | --- | --- |
| LOXDG697U | 5'-697 | 23 | CCNTAYCCNMGNMGNGGNMGNAC SEQ ID NO: 5 |
| LOXDG1081U | 5'-1081 | 23 | ACNGAYGARGARTTYGCNMGNGA SEQ ID NO: 6 |
| LOXDG1081L | 3'-1081 | 23 | TCNCKNGCRAAYTCYTCRTCNGT SEQ ID NO: 7 |
| LOXDG1522U | 5'-1522 | 22 | WSNCAYTGGYTNAAYACNCAYG SEQ ID NO: 8 |
| LOXDG1552L | 3'-1555 | 22 | CNGCRTGNGTRTTNARCCARTG SEQ ID NO: 9 |
| LOXDG2128L | 3'-2128 | 23 | TGNCCRAARTTNACNGCNGCRTG SEQ ID NO: 10 |

N = A or G or C or T
W = A or T
Y = C or T
M = A or C
K = G or T
R = A or G
S = G or C

The primers were used in the combinations set out below:

1) LOXDG697U with LOXDG1081L
2) LOXDG697U with LOXDG1552L
3) LOXDG697U with LOXDG2128L
4) LOXDG1081U with LOXDG1552L
5) LOXDG1081U with LOXDG2128L
6) LOXDG1522U with LOXDG2128L PCR reactions were carried out using Amplitaq DNA polymerase from PE Applied Biosystems (Foster City, Calif.) following the manufacturers recommended protocol. Briefly, each reaction contained 5 uL of 10×PCR buffer, 0.25 uL of Amplitaq DNA polymerase, 1 uL of 10 mM dNTPs, 1 uL of each primer (approximately 50 uM), 5 uL of template and 36.75 uL of DDH2O for a final volume of 50 uL. Four different cDNA libraries (Vitis cinerea leaf, Vitis vinifera cv. Cabernet sauvignon leaf, stem and cambium) and Vitis vinifera cv. Cabernet sauvignon genomic DNA were used as templates.

PCR was carried out using a PE Applied Biosystems 9600 Thermocycler using a 3-step PCR sequence as follows: (1) an initial denaturation step of two minutes at 95° C. followed by 35 cycles of (2) denaturation for 30 seconds at 95° C., (3) hybridization for 40 seconds at an annealing temperature; and (4) primer extension for two minutes at 72° C. The amplification product was (5) held for ten minutes at 72° C. and then (6) held at 4° C.

Initial annealing temperatures were 45° C., 50° C., 55° C. and 60° C. In the initial experiments, multiple bands were seen at 45° C. with primer combinations 2 and 6 with all samples. No amplification was seen with other primer combinations. Similar results were seen at 50° C. The only combination of temperature and primers that produced the expected size range fragment was LOX 1081U with LOX 2128L at 55° C. with the Vitis vinifera cv. Cabernet sauvignon genomic DNA. The amplified fragments were cloned into TA cloning vectors, (Invitrogen Inc. Carlsbad, Calif.) and sequenced using an ABI 377 automated fluorescent sequencer (PE Applied Biosystems, Foster City, Calif.). Sequencing kits, Big Dye, (PE Applied Biosystems, Foster City, Calif.) were used for all sequencing at one fourth the manufacturer's suggested volume.

Clone 10 from Vitis vinifera cv. Cabernet sauvignon genomic DNA was the only clone that had DNA sequence with homology to known lipoxygenase genes. This clone comprised LOX genomic Clone 10 forward sequencing primer having 639 nucleotides:

(SEQ. ID NO:11)
TACGACTCACTATAGGGCGAATTGGGCCCTCTAGATGCATGCTCGAGCGG

CCGCCAGTGTGATGGATATCTGCAGAATTCGGCTTACGGATGAGGAGTTT

GCGCGGGAAATGCTGGCTGGACTCAACCCAGTTGTCATCCGACTACTCCA

AGTAAACTACAGCTTCCTTTCAAATAATTTTTAATGCCCTGTTTGTTTTC

TGAGAAAATGGAACTTGGAAAGGCTTCCAGACTTTGTTTTCTTTCCCTCC

ATCTACTGTTCTAGCTCTTTTCTGATAATTATTGTCTTTCTATTTTGTTT

GAAGGAGTTTCCTCCAAAAAGCAAGCTGGATCCTGAAGTTTATGGCAACC

AAAACAGTTCAATAACCAAAGAACACATAGAGAATCACCTGGATGACCTT

ACTATAAACGAGGTAACGCTCTTAGGTTCCCTTCTTTCAAACTAAATTTT

TCAATGTCGACATGTTAATTTTTTGCATTGGrACACAAGCCATAGTAACT

GAAAAATGGTGCGTTTTACTAAGGCAATGGAGAAGAAGAGGCTATTCATA

TTAAATCACCATGATGTTTTCATGCCATACCTGAGGAGGATAAACACAAC

TTCCACGAAAACATACGCCTCAAGGACTCTCCTCTTCCT

The clone also comprised a LOX genomic Clone 10 reverse sequencing primer having 636 nucleotides:

(SEQ ID NO:12)
TCAAGCTTGGTACCGAGCTCGGATCCACTAGTAACGGCCGCCAGTGTGCT

GGAATTCGGCTTTGGCCGAAATTGACGGCGGCGTGGAGAGCAGAAGCCAC

CCAGATGATAATGGTGCATGTTTCTATCAGCTCTTTGACAGTACGCATTT

-continued

TAGGCCACCAAGGCTCGTCCTTCTTGTCGCCATGACCCTCTTCCCTGACT

TCCTTCCACCAGGACTGAAGCTCAGAGTCTTTCTGGACCATCTCATCTGT

CTTGTAGTAGAATGAGCAATACTCTTTCACCCATGTCTCAATAGCTGACC

AGATCTCAAGTCCATCAACAGCATAGGGGTAGTCATCTATCAGTAGGCGG

AGTCCATGAGGGGCCTCTGAATCCTCAACCGCCATTCCTCTGAAAGAGTG

CCCAAGTTGGAGCATATCAGTTAGATGAAAATCACAATTTTCACTAGATT

CATTGCACAGCAGGAAAGAAAACAATCACTAACAGTATTTATATACCTCT

TGATGAGATCAGCAGGAAGTGCTTGCTCAGTGAGAACCCAGTCTTTGTAA

ACAACAGATGACATTTCCATGGCATACTTTGATGGAAAAACTGTGCTCTC

CACCACTCCACCAGCATTGATGAGGATTTGTCGAGC

The two sequences do not overlap, as the original amplification product was approximately 1500 nucleotides.

EXAMPLE 2

LOX primers were designed based on the *Vitis vinifera* cv. *Cabernet Sauvignon* DNA sequence of Example 1. These primers should amplify a LOX gene in Vitis sp. genomic DNA. The primary goal was to link the two segments of DNA sequence and obtain a contiguous Vitis LOX genomic sequence spanning 1200–1500 nucleotides. In addition it was intended to extend the sequence in the 3' and 5' directions.

Primers were designed based upon the genomic DNA sequence and are listed in Table 6 below:

TABLE 6

| Printer Name | Starting Nucleotide | Primer Length | Sequence 5'-3' |
| --- | --- | --- | --- |
| LOX1 ExtL | 3'-315 | 23 | TTC AGG ATC CAG CTT GCT TTT TG (SEQ ID NO:13) |
| LOX2 IntL | 3'-600 | 23 | TGA GGC GTA TGT TTT CGT GGA AG (SEQ ID NO:14) |
| LOX2 ExtU | 5'-594 | 23 | ACA CAA CTT CCA CGA AAA CAT AC (SEQ ID NO:15) |
| LOX3 IntU | 5'-649 | 23 | ATC CTC ATC AAT GCT GGT GGA GT (SEQ ID NO:16) |
| LOX1 IntU | 5'-315 | 23 | CAA AAA GCA AGC TGG ATC CTG AA (SEQ ID NO:17) |
| LOX3 ExtL | 3'-669 | 20 | AAA CTG TGC TCT CCA CCA CT (SEQ ID NO:18) |
| LOX4 ExtU | 5'-1090 | 23 | GTC ATG GCG ACA AGA AGG ACG AG (SEQ ID NO:19) |
| LOX4 IntL | 3'-1092 | 20 | TCG TCC TTC TTG TCG CCA TG (SEQ ID NO:20) |

Initial PCR experiments were conducted with a 55° C. annealing temperature and the same templates and thermocycler program as used in Example 1 above using the primers in the following combinations:

1) LOX1 IntU with LOX2 IntL
2) LOX1 IntU with LOX3 ExtL
3) LOX1 IntU with LOX4 IntL
4) LOX1 ExtL with Vector TX5'
5) LOX2 IntL with Vector TX5'
6) LOX3 ExtL with Vector TX5'
7) LOX4 IntL with Vector TX5'
8) LOX2 ExtU with LOX3 ExtL
9) LOX2 ExtU with LOX4 IntL
10) LOX3 IntU with LOX4 IntL
11) LOX3 IntU with Vector TX3'
12) LOX4 ExtU with Vector TX3'

The amplification products were sequenced and analyzed. Some of the primers did not amplify any cDNAs indicating that they were probably located in intron regions of the genomic DNA. New primers were synthesized. Primer LOX 69IntU starting at nucleotide 5'-69 and having the sequence GAT GTT TTC ATG CCA TAC CTG AG (SEQ ID NO: 21) and primer LOX 1307IntL starting at nucleotide 3'-1307 and having the sequence TTG CCA GTA AGC CCA CCT T (SEQ ID NO: 22) were synthesized. The use of these primers in a PCR reaction resulted in amplification of the entire region between the primers yielding 1398 bases of continuous sequence from the *Vitis vinifera* cv. *Cabernet Sauvignon* stem cDNA library and having the sequence:

(SEQ ID NO:23)
TGGCATGAAACATCAAACTACGCCTCAAGGACTCTCCTCTTCCTGAAAGA

CGACGGAACTTTGAAGCCGCTGGCGATTGAATTGAGCCTACCACATCCTA

ATGGGGATAAATTCGGAGCTGTCAACAAAGTATACACACCAGCTGAAGAT

GGCGTTGAAGGTTCCATTTGGCAGCTGGCTAAAGCTTATGCTGCTGTGAA

TGACTCTGGCTATCATCAGCTCCTCAGCCACTGGTTGAATACACATGCTG

CAATTGAGCCATTTGTGATTGCAACCAACAGGCAGCTCAGTGTGCTTCAC

CCAATTCACAAGCTTTTGCATCCTCACTTCCGTGATACGATGAATATAAA

-continued
TGCATTAGCTCGACAAATCCTCATCAATGCTGGTGGAGTGGTGGAGAGCA

CAGTTTTTCCATCAAAGTATGCCATGGAAATGTCATCTGTTGTTTACAAA

GACTGGGTTCTCACTGAGCAAGCACTTCCTGCTGATCTCATCAAGAGAGG

AATGGCGGTTGAGGATTCAGAGGCCCCTCATGGACTCCGCCTACTGATAG

ATGACTACCCCTATGCTGTGATGGACTTGAGATCTGGTCAGCTATTGAGA

CATGGGTGAAAGAGTATTGCTCATTCTACCACAAGACAGATGAGATGGTC

```
-continued
CAGAAAGACTCTGAGCTTCAGTTCTGGTGGAAGGAAGTCAGGGAAGAGGG

TCATGGCGACAAGAAGGACGAGCCTTGGTGGCCTAAAATGCGTACTGTCA

AAGAGCTGATACAAACATGCACCATTATCATCTGGGTGGCTTCTGCTCTC

CATGCTGCAGTGAATTTCGGGCAGTACCCTTATGCAGGCTACCTCCCAAA

CCGCCCAACGATAAGCCGCAGATTCATGCCTGAAGAAGGCACTCCTGAGT

ATGAAGAACTCAAGTCCAATCCTGATAAGGCTTTCCTGAAAACAATCACT

GCCCAGCTGCAGACCCTTCTTGGCATCTCCCTTATTGAGGTCCTTTCCAG

GCATTCTTCCGATGAGGTTTATCTTGGACAGAGAGACACTCCTGAATGGA

CCCTGGACGCAACACCATTGAAAGCTTTTGAGAAATTCGGAAGGAAGCTG

GCAGACATTGAAGAGAGGATCATAGATAGAAATGGAAATGAGAGATTCAA

GAACAGAGTTGGGCCTGTGAAGATACCATACACTGTTATGATGCCA
```

EXAMPLE 3

According to this example, complete LOX DNA genomic sequences were isolated from *Vitis vinifera* by screening a *Vitis vinifera* cv. *Cabernet Sauvignon* genomic library constructed using the Bacterial Artificial Chromosome vector, pECBAC1. Briefly, high molecular weight (HMW) DNA was obtained using isolated nuclei embedded in agarose plugs. The HMW DNA was partially digested with Bam HI or Eco RI restriction endonuclease, and size-fractioned by pulsed- field electrophoresis. The region of the gel containing HMW DNA from 150–250, 250–350, and 350–450 kb was excised, and subjected to a second selection using pulsed- field electrophoresis. The second size selection products were excised from the gel and electroeluted from the gel fragments in dialysis tubing. The HMW DNA fractions were then dialyzed overnight, and then ligated into pECBAC1 vector. The ligation mix was used to transform electrocompetent *Escherichia coli* DH10B cells (ElectroMAX, Gibco BRL, Grand Island, N.Y.) using a BioRad Gene Pulser II electroporator (BioRad Inc., Hercules, Calif.). Transformed bacteria were selected on Luria Broth (LB) plates containing chloramphenicol, and bacteria with inserts detected by blue/white selection using X-gal and IPTG. The library was plated onto 20×20 cm bioassay trays (Genetix Ltd, Dorset, UK) and picked into 384-microwell plates using a QPIX robotic picker (Genetix Ltd., Dorset, UK). The library was arrayed onto nylon membranes using the QPIX (Genetix Ltd., Dorset, UK) gridding software package at a density of about 10,000 cDNAs/filter.

Probes derived from the sequenced Vitis LOX gene (SEQ ID NO: 23) and described in Example 2, were used to screen the nylon membranes. Briefly, the PCR product was isolated from an agarose gel by the band intercept method using NA 45 DEAE membranes (Schleicher and Schuell, Keene, N. H.). One microgram of purified insert was labeled separately for each, using the DIG High Prime DNA labeling and detection starter kit (Roche Molecular Biochemicals, Mannheim Germany). The BAC library membranes were prehybridized at 42° C. for 30 min using the DIG Easy Hyb hybridization solution provided in the kit. The probe was denatured and added to 5 ml of hybridization solution. The prehybridization solution was poured off and the probe solution was added. The BAC library filters were incubated with the probe at 42° C. in a VWR rotating hybridization oven overnight. The library membranes were washed and blocked according to the labeling kit protocols, with the following stringency's; 2×SSC, 0.1% SDS for 5 min at 27° C., and 0.5× SSC, 0.1% SDS for 20 min at 65 C. The membranes were exposed to Kodak BioMax double emulsion film for 4 hours before developing.

Eighteen clones were identified, isolated, and arrayed on a new membrane, and screened a second time with the LOX probe. Individual clones that tested positive the second trial were categorized as LOX containing BAC sequence. Fifteen clones were archived, and then cultured for plasmid isolation. Plasmids were isolated using the Qiagen Large-Construct Kit following manufacturers instructions (Qiagen Inc., Valencia, Calif.). Of these, the clone, LOX BAC D2, was modified using the Epicentre EZ::TN Transposon <KAN-2> insertion kit (Epicentre Technologies Corp., Madison, Wis.). Briefly, the purified clone plasmid was combined with the EZ::TN transposon and transposase enzyme, then incubated for two hours at 37° C. The reaction mixture was used to transform electrocompetent Escherichia coli DH10B cells (ElectroMAX, Gibco BRL, Grand Island, N.Y.) using a BioRad Gene Pulser II electroporator (BioRad Inc., Hercules, Calif.). Transformed bacteria were plated on Luria Broth (LB) plates containing kanamycin to select LOX BAC clones containing randomly inserted EZ::TN <KAN-2> transposon. Individual clones were isolated, and bidirectionally sequenced using the two primer sites on the transposon per the manufacturer's instruction. Sequencing was done using an ABI 377 automated fluorescent sequencer (PE Applied Biosystems, Foster City, Calif.), and Big Dye sequencing kits (PE Applied Biosystems, Foster City, Calif.) were used at one fourth the manufacturer's suggested volume. Sequence derived from the individual clones was matched to known sequences using the BLAST algorithm. Sequences with homology to known lipoxygenase were archived and screened for redundancy. Fifteen unique lipoxygenase sequences were identified in the first group of 96 clones sequenced. These sequences were aligned with the Prunus dulcis genomic DNA sequence in the public databases, to determine fragment order and alignment. Initial analysis indicated the sequences were located randomly, across a region spanning approximately 4 kb (1590–5610) of the Prunus dulcis LOX gene.

The following primers were designed (OLIGO 5.0 Primer Analysis Software, National BioSciences Inc., Plymouth, Minn.) to sequence the contiguous internal sequence, as well as adjacent external sequence; 48L, 27U, 69L, 1380L, 1361U, 117L, 97U, 1167L, 1146U, 123U, 145L, 625U, 940L, 950L,1036U, 1697U, and 1018L. All 15 of the Vitis LOX containing BAC clones were used as template for sequencing reactions. Sequencing was done using an ABI 377 automated fluorescent sequencer (PE Applied Biosystems, Foster City, Calif.), and Big Dye sequencing kits (PE Applied Biosystems, Foster City, Calif.) were used at one fourth the manufacturer's suggested volume. Internal and external sequence was obtained using the initial primers. Sequence from the 5' end of the LOX gene resulted in poor quality sequence. Analysis of the data indicated the 5' sequencing primer was annealing in more than one location on the BAC template. In addition, there were heterozygous regions of DNA in the internal LOX fragment sequence. In order to avoid the problems associated with sequencing directly from the BAC vectors, a different approach, involving cloning PCR product amplified with pairs of the sequencing primers was initiated. PCR reactions were done using Amplitaq Gold DNA polymerase (PE Applied Biosystems, Foster City, Calif.) following the manufacturers recommended protocol. Briefly, each reaction contained 5 uL of 10×PCR buffer, 0.25 uL of Amplitaq DNA polymerase, 1 uL of 10 mM dNTPs, 1 uL of each primer (approximately 50 uM), 5 uL of template and 36.75 uL of DDH2O for a final volume of 50 uL. PCR was carried out using a PE Applied Biosystems 9600 Thermocycler using a 3-step PCR sequence as follows: (1) an initial denaturation step of ten minutes at 95 C. followed by 35 cycles of (2) denaturation for 30 seconds at 95 C., (3) hybridization for 40 seconds at a 50–60 C. (primer dependent) annealing temperature; and (4) primer extension for two minutes at 72 C. The amplification product was (5) held for ten minutes at 72 C. and then (6) held at 4 C. The PCR products were run on 1.0% agarose gels (Molecular Biology Grade Agarose, AMRESCO) and target bands were isolated from the gels by the band intercept method using NA 45 DEAE membranes (Schleicher and Schuell, Keene, NH). Primers 27U and 1036 L were used to amplify a 2.8 kb fragments from all 15 Vitis LOX containing BAC clones, which were cloned using the Topo-TA cloning kit according to manufacturer's instructions (Invitrogen Corp. Carlsbad, Calif.). Individual clones were sequenced using an ABI 377 automated fluorescent sequencer (PE Applied Biosystems, Foster City, Calif.), and Big Dye sequencing kits (PE Applied Biosystems, Foster City, Calif.) were used at one fourth the manufacturer's suggested volume. Sequence was assembled using Sequence Navigator v1.01 (PE Applied Biosystems, Foster City, Calif.), until the complete 2.8 kb Vitis LOX sequence was obtained. Sequence analysis and comparison among the clones indicated several variants, of the LOX gene were present. PCR product from primer pair 1697U and 48L was used to obtain clones containing sequence in the 5' direction from the 2.8 Kb fragment and approximately 1.3 kb of sequence was obtained. Primer 1697U was then used with primer 1307L to amplify the entire 4.1 Kb Vitis LOX gene fragment. The fragment was amplified and cloned using the Topo-TA cloning kit according to manufacturer's instructions. Sequence analysis and comparison among the clones indicated at least three variants, of the LOX gene were present. The 4.1 Kb fragment contained part of the first exon, as well as the remaining 8 exons present in the Vitis LOX gene. There was evidence indicating the different LOX genes were arrayed close together in a tandem pattern. External primers 1018U, 6588U and 145L were designed (OLIGO 5.0 Primer Analysis Software, National BioSciences Inc., Plymouth, Minn.) from the Vitis LOX sequence in an attempt to amplify intergenic regions between adjacent LOX genes. PCR product was cloned using the Topo-TA cloning kit according to manufacturer's instructions. Individual clones were sequenced using an ABI 377 automated fluorescent sequencer (PE Applied Biosystems, Foster City, Calif.), and Big Dye sequencing kits (PE Applied Biosystems, Foster City, Calif.) were used at one fourth the manufacturer's suggested volume. Sequence was aligned using Sequence Navigator v1.01 (PE Applied Biosystems, Foster City, Calif.), and compared to LOX sequence in public databases and Vitis Lox sequence genevaled as part of the invention. Several clones had sequence on both ends of the clone with homology to LOX, indicating a cloned intergenic region. These cloned intergenic regions contained DNA sequence from the ninth and final exon of Vitis LOX, and from the first exon of Vitis LOX. Between the end sequences was a region containing both the 3' and 5' untranslated regions, which had no homology to any known sequences in the public databases. These results confirmed that there were three Vitis LOX genes organized in a tandem array. Lastly, the Genome Walker kit (Clontech Laboratories Inc., Palo Alto, Calif.) was used to extend sequence data in the 5' direction in an attempt to clone the 5' untranslated region of the first LOX gene in the array. LOX specific primers 2953L, 3020L, 3406L and 3461L were designed (OLIGO 5.0 Primer Analysis Software, National BioSciences Inc., Plymouth, Minn.) and used in conjunction with primers in the kit as per the manufacturer's instructions. Analysis of the DNA sequence obtained from this method failed to obtain the 5' end of the first LOX gene in the array, but confirmed the two intergenic regions identified earlier.

TABLE 7

Vitis genomic sequencing and PCR primers

| | |
|---|---|
| LOX 1018U | SEQ ID NO:24 CTACCTCCCAAACCGCCCA |
| LOX 1036L | SEQ ID NO:25 TGGGCGGTTTGGGAGGTAG |
| LOX 1146U | SEQ ID NO:26 TTCTTGGCATCTCCCTTATTGA |
| LOX 1167L | SEQ ID NO:27 TCAATAAGGGAGATGCCAAGAA |
| LOX 117L | SEQ ID NO:28 TGACCTTGAATGCAGACTCGC |
| LOX 123U | SEQ ID NO:29 GACTGGGATGAGGAGATTGGAGA |
| LOX 1361U | SEQ ID NO:30 ACACTGCTCTACCCCACAAG |
| LOX 1380L | SEQ ID NO:31 CTTGTGGGGTAGAGCAGTGT |
| LOX 145L | SEQ ID NO:32 TCTCCAATCTCCTCATCCCAGTC |
| LOX 1697U | SEQ ID NO:33 CATGGTGATCCTGGTGAGTT |
| LOX 27U | SEQ ID NO:34 TTACAGGGGAAAATTGGAAAAC |
| LOX 2953L | SEQ ID NO:35 CCAAGTATGCTGGTTTTCCAATTTTCC |
| LOX 3020L | SEQ ID NO:36 CAGTCGAACGTGACCTTGAATGCAGAC |
| LOX 3406L | SEQ ID NO:37 CTGTACTTGCGCAGTGGCCCTGGTGTT |
| LOX 3461L | SEQ ID NO:38 CCATTCCTTAAGCTCTCCGGTTCCATC |
| LOX 48L | SEQ ID NO:39 GTTTTCCAATTTTCCCCTGTAA |
| LOX 625U | SEQ ID NO:40 ATATGATTGATTTCTGCTCTT |
| LOX 6588U | SEQ ID NO:41 GTCCATTTGAAGAAGTGTGAGAC |
| LOX 69L | SEQ ID NO:42 CTCAGGTATGGCATGAAAACATC |
| LOX 940L | SEQ ID NO:43 AGCATTGATGAGGAATTTGTCG |
| LOX 950L | SEQ ID NO:44 CCACTCCACCAGCATTGATG |
| LOX 97U | SEQ ID NO:45 GCGAGTCTGCATTCAAGGTCA |

Vitis LOX sequences were analyzed and assembled using Sequence Navigator v1.01 (PE Applied Biosystems). Two complete and unique Vitis LOX gene sequences were identified (SEQ ID 2 and SEQ ID 4). GENSCAN analysis software (GENSCAN Server, Massachusetts Institute of Technology, Cambridge, Mass.) was used to determine the gene structure, including exons, introns, and the predicted amino acid sequence. Both Vitis LOX genes contained 9 exons, as does the *Prunus Dulcis* LOX gene. In addition, the predicted amino acid structures are 96% identical to each other (SEQ ID 1 and SEQ ID 3), whereas the closest homology to another species is 76% and 78% to the Prunus LOX, for Vitis LOX SEQ ID 1 and 3 respectively.

Vitis LOX 1 Amino acid sequence (SEQ ID NO: 1)
MKKKLLSIVSAITGENDKKKIEGTIVLMKKNVLDFNDFNAPVRDRVHELF
GQGVSLQLVSAVHGDPANGLQGKLGKPAYLEDWITTITSLTAGESAFKVT
FDWDEEIGEPGAFIIRNNHHSEFYLRTLTLEDVPGRGRIHFVCNSWVYPA
KHYKTDRVFFTNQTYLPSETPGPLRKYRKGELVNLRGDGTGELKEWDRVY
DYAYYNDLGKPDRDLKYARPVLGGSAEYPYPRRGRTGRPPSEKDPKTESR
LPLVMSLNIYVPRDERFGHLKMSDFLAYALKSIVQFLLPEFEALCDITPN
EFDSFQDVLDLYEGGIKVPEGPLLDKIKDNIPLEMLKELVRTDGEHLFKF
PMPQVIKEDKSAWRTDEEFAREMLAGLNPVVIRLLQEFPPKSKLDPEVYG
NQNSSITKEHIENHLDDLTINEAMEKKRLFILDHHDVFMPYLRRINTTST
KTYASRTLLFLKDDGTLKPLAIELSLPHPNGDKFGAVNKVYTPAEDGVEG
SIWQLAKAYAAVNDSGYHQLLSHWLNTHAAIEPFVIATNRQLSVLHPIHK
LLHPHFRDTMNINALARQILINAGGVVESTVFPSKYAMEMSSVVYKDWVL
TEQALPADLIKRGMAVEDSEAPHGLRLLIDDYPYAVDGLEIWSAIETWVK
EYCSFYYKTDEMVQKDSELQSWWKEVREEGHGDKKDEPWWPKMRTVKELI
ETCTIIIWVASALHAAVNFGQYPYAGYLPNRPTISRRFMPEEGTPEYEEL
KSNPDKAFLKTITAQLQTLLGISLIEVLSRHSSDEVYLGQRDTPEWTLDT
TPLKAFEKFGRKLADIEEMIIDRNGNERFKNRVGPVKIPYTLLYPTSEGG
LTGKGIPNSVSI Vitis LOX 1 sequence (SEQ ID NO: 2)
ATGAAGAAGAAGCTTCTTTCAATTGTTAGTGCCATCACTGGGGAAAATGA
TAAGAAGAAGATCGAGGGAACTATTGTGTTGATGAAGAAGAATGTGTTGG
ATTTTAATGACTTCAATGCACCGGTTCGGGACCGGGTTCATGAGCTTTTT
GGACAGGGAGTCTCTCTGCAGCTCGTCAGTGCTGTTCATGGTGATCCTGG
TGAGTTTTTTTTTTTTTTTTTCCTTCATGTTTTTGATGATGGGGTTGT
TGAAGTTGGAGGAGAGGAGGTTGATACCGTTTTGTGAGGGTGAGATGGGT
TCTGAATTTTGATGATAGCAATTGGAAAAAGATGTGATTTTTGGAAGAGG
CCAAGAGGGGTTGTTATTCTCAGAGATGAGTCAAATGACTTTCTTGACAT
CTTCCATTCAACTGGGCACTTTTCTAACTGCTTTTGTTTTTTGTGTTTTG
TTTTTAATGCTTTTGTTTTCTACTTCTTTCTCTTGTTTATATTTCTTTTC
ATCAACCACTATACATGCCCACCTAACTCAATATGAAATTCCCATGCAGC
TGCCCTTTTTTTAAGCCACTAGATCTTGGGTGATTTTTTAGTCTTAGAT
CTTGGGTTAGATTTCCCCAGATTTCACAAAAGTTGAAACTGAAATTCATA
AAATTTTTGAGGATCACTCCTGTTGGAGTTAAAGAGAAAGAATTGCCATA
AACCAAGGAGATGAATTGTTGTGAAATATTTCTCAAAACTTCATCATCAA
ATACCTGCCAAAACAGCCACAGTTTCTGAAATTTCATGCAGCAAAGCCAC
TGCTGCTTGTAGCAAGTCCAAGCTCAAACATAAAAGCCTTTTCAACCCAG
TGATTTTTGAGAATAACATGTAAAAATGCAGTGACCATCTGTTAGTGATG
ATATTGAACTTGTGTGCCTTTTGTAGCAAATGGGTTACAGGGGAAACTTG
GGAAACCAGCATACTTGGAAGACTGGATTACCACAATTACTTCTTTAACC
GCTGGCGAGTCTGCATTCAAGGTCACGTTCGACTGGGATGAGGAGATTGG -continued
AGAGCCAGGGGCATTCATAATTAGAAACAATCACCACAGTGAGTTTTACC
TCAGGACTCTCACTCTTGAAGATGTTCCTGGACGTGGCAGAATTCACTTT
GTTTGTAATTCCTGGGTCTACCCTGCTAAGCACTACAAAACTGACCGTGT
TTTCTTCACTAATCAGGTAAGACTAATTTGCTTGATACTAGGAGAGTCTG
CTGTGGCATTGTGGCCCATTGAGCTTAGGCAAGGAGAATTGTCTGCTAAA
GGAATGTGTTTATTTTATCTGCTGCAGACATATCTTCCAAGTGAAACACC
AGGGCCACTGCGCAAGTACAGAAAAGGGGAACTGGTGAATCTGAGGGGAG
ATGGAACCGGAGAGCTTAAGGAATGGGATCGAGTGTATGACTATGCTTAC
TATAATGATTTGGGGAAGCCAGACAGGGATCTCAAATATGCCCGCCCTGT
GCTGGGAGGATCTGCAGAGTATCCTTATCCCAGGAGGGGAAGAACTGGTA
GACCACCATCTGAAAAAGGTAGATATTTGATACACAAATTCATATTGTTT
CTCATGCTTTTATCATAAAAGGATGAATATGATTGATTTCTGCTCTTCTT
TTAATTAACAGATCCCAAAACTGAGAGCAGATTGCCACTTGTGATGAGCT
TAAACATATATGTTCCAAGAGATGAACGATTTGGTCACCTGAAGATGTCA
GACTTCCTGGCTTATGCCCTGAAATCCATAGTTCAATTCCTCCTCCCTGA
GTTTGAGGCTCTATGTGACATCACCCCCAATGAGTTTGACAGCTTCCAAG
ATGTATTAGACCTCTACGAAGGAGGAATCAAGGTCCCAGAGGGCCCTTTA
CTGGACAAAATTAAGGACAACATCCCTCTTGAGATGCTCAAGGAACTTGT
TCGTACCGATGGGAACATCTCTTCAAGTTCCCAATGCCCCAAGTCATCA
AAGGTACTGCATACATCTAACATCTTGTAATCTTTGAAGCCAGATTTATA
TATTTATTTTTCATAAAATTGATGACGTTTTTATCATGCTGGAGCAGAGG
ATAAGTCTGCATGGAGGACTGACGAAGAATTTGCTAGAGAAATGCTGGCT
GGACTCAACCCAGTTGTCATCCGTCTACTCCAAGTAAACTACAGCTTCCT
TTCAAATAATTTTTAATGCCCTGTTTGTTTTCTGAGAAAATGGAACTTGG
AAAGGCTTCCAGACTTTGTTTTCTTTCCCTCCATCTACTGTTCTAGCTCT
TTTCTGATAATTATTGGCTCTTTCTACTTTGTTTGAAGGAGTTTCCTCCA
AAAAGCAAGCTGGATCCTGAAGTTTATGGCAACCAAAACAGTTCAATAAC
CAAAGAACACATAGAGAATCACCTGGATGACCTTACTATAAACGAGGTAA
CGCTCTTAGGTTCCGTTCTTTCAAACTAAATTTTTCAATGTCGACATGTT
AATTTTTTGCATTGGAACACAAGCCATAGTAACTGAAAAATGGTGCTTTT
TACTAGGCAATGGAGAAGAAGAGGCTATTCATATTAGATCACCATGATGT
TTTCATGCCATACCTGAGGAGGATAAACACAACTTCCACGAAAACTTACG
CCTCAAGGACTCTCCTCTTCCTGAAAGACGACGGAACTTTGAAGCCACTG
GCGATTGAATTGAGCCTACCACATCCTAATGGGATAAATTCGGAGCTGT
CAACAAAGTATACACACCAGCTGAAGATGGCGTTGAAGGTTCCATTTGGC
AGCTGGCTAAAGCTTATGCTGCTGTGAATGACTCTGGCTATCATCAGCTC
CTCAGCCACTGGTACGTAATCTCCCAAAGGAAAGTGCGTACAGTTGGGGC
GTAAATCTGAAGCGGGTTATGAATATCTTTGATGTTGGTTGCAGGTTGAA
TACACATGCTGCAATTGAGCCATTTGTGATTGCAACCAACAGGCAGCTCA
GTGTGCTTCACCCAATTCACAAGCTTTTGCATCCTCACTTCCGTGATACG

```
ATGAATATAAATGCATTAGCTCGACAAATCCTCATCAATGCTGGTGGAGT
GGTGGAGAGCACAGTTTTTCCATCAAAGTATGCCATGGAAATGTCATCTG
TTGTTTACAAAGACTGGGTTCTCACTGAGCAAGCACTTCCTGCTGATCTC
ATCAAGAGGTATATAAATACTGTTAGTGATTGTTTTCTTTCCTGCTGTGC
AATGAATCTAGTGAAAATTGTGATTTTCATCTAACTGATATGCTCCAACT
TGGGCACTCTTTCAGAGGAATGGCGGTTGAGGATTCAGAGGCCCCTCATG
GACTCCGCCTACTGATAGATGACTACCCCTATGCTGTTGATGGACTTGAG
ATCTGGTCAGCTATTGAGACATGGGTGAAAGAGTATTGCTCATTCTACTA
CAAGACAGATGAGATGGTCCAGAAAGACTCTGAGCTTCAGTCCTGGTGGA
AGGAAGTCAGGGAAGAGGGTCATGGCGACAAGAAGGACGAGCCTTGGTGG
CCTAAAATGCGTACTGTCAAAGAGCTGATAGAAACATGCACCATTATCAT
CTGGGTGGCTTCTGCTCTCCATGCTGCAGTGAATTTCGGGCAGTACCCTT
ATGCAGGCTACCTCCCAAACCGCCCAACGATAAGCCGCAGATTCATGCCT
GAAGAAGGCACTCCTGAGTATGAAGAACTCAAGTCCAATCCTGATAAGGC
TTTCCTGAAAACAATCACTGCCCAGCTGCAGACCCTTCTTGGCATCTCCC
TTATTGAGGTCCTTTCCAGGCATTCTTCCGATGAGGTTTATCTTGGACAG
AGAGACACTCCTGAATGGACCCTGGACACAACACCATTGAAAGCTTTTGA
GAAATTCGGAAGGAAGCTGGCAGACATTGAAGAAATGATCATAGATAGAA
ATGGAAATGAGAGATTCAAGAACAGAGTTGGGCCTGTGAAGATACCATAC
ACACTGCTCTACCCCACAAGCGAAGGTGGGCTTACTGGCAAAGGGATTCC
CAACAGTGTCTCCATCTAAATTTTCCTGGAAAATCATGAGCACACTGCTG
ATCAAGATGCTTAAATGCACATTGCTAATATAGTATACTGTAATTTATA
ATACCTATTTTTCGACTTTGTAGGATTCATATTGATGCATATATTTATAA
TAAGGAATTATTTATTGCTAGAAAATTGGGAGCTTTTCACTTTTTTTATG
ATCTGTGCCACACTTAATGTTAAAAGATGAAGGTGAAGTAGCAAAACAGT
TGATCTGAATGCGCAGCCATTGATATCAGGAATCAAAGTCAGATGGTGCA
AATGCTCTCAAAACATCCACCCTCCCACAAAATTATCTATAATTTACATG
TTAACAAGAACTCAAGAGTGAGTAAGAAACTATGTTGAGAAATACTTTCT
GAAACCACTGAGGAAAGTGTCCATTTGAAGAAGTGTGAGACTCTTACCTA
AGAAGTGTCTGTAGATTTGAATAGTAACTGCCAATATCTCTATCAAATCT
TTATTATTACATGTATTAGATTTTGATATGATGCTTGGATAGTATGCCTA
TAAACAAATGCATCCCCGAGCTTCTTCTTTGTATATTCTTCTGCTCTCAC
ATTCTTGGCTTTCTTCTGCTTAGCTTTGTTGTTGTTG
```

Vitis LOX 2 amino acid sequence (SEQ ID NO: 3)
MIHSIVGAITGENDKKKIKGTVVLMKKNVLDFNDFNASVLDRVHELLGQG
VPLQLVSAVHGDPANGLQGKIGKPAYLEDWITTITSLTAGESAFKVTFDW
DEEIGEPGAFIIRNNHHSEFYLRTLTLEDVPGRGRTHFVCNSWVYPAQHY
KTDRVFFTNQTYLPSETPGPLRKYREGELVNLRGDGTGELKEWDRVYDYA
YYNDLGNPDRDLKYARPVLGGSAEYPYPRRGRTGRPPSEKDPNTESRLPL
VMSLNIYVPRDERFGHLKMSDFLAYALKSIVQFLLPEFEALCDITHNEFD
SFQDVLDLYEGGIKVPEGPLLDKIKDNIPLEMLKELVRTDGEHLFKFPMP
QVIKEDKSAWRTDEEFAREMLAGLNPVVIRLLQEFPPKSKLDPEVYGNQN
SITKEHIENHLDDLTINEAMEKKRLFILDHHDVFMPYLRRINTTSTKTYA
SRTLLFLKDDGTLKPLAIELSLPHPSGDKFGAVNKVYTPAENGVEGSIWQ
LAKAYAAVNDSGYHQLLSHWLNTHAAIEPFVIATNRQLSVLHPIHKLLHP
HFRDTMNINALARQILINAGGVVESTVFPSKYAMEMSSVVYKDWVLTEQA
LPADLIKRGMAVEDSEAPHGLRLLIDDYPYAVDGLEIWSAIETWVKEYCS
FYYKTDEMVQKDSELQSWWKEVREEGHGDKKDEPWWPKMHTVKELIETCT
IIIWVASALHAAVNFGQYPYAGYLPNRPTISRRFMPEEGTPEYEELKSNP
DKAFLKTITAQLQTLLGISLIEVLSRHSSDEVYLGQRDTPEWTLDTTPLK
AFEKFGRKLADIEEMIIDRNGNERFKNRVGPVKIPYTLLYPTSEGGLTGK
GIPNSVSI Vitis LOX 2 Sequence (SEQ ID NO:4)
```
ATGATTCATTCAATTGTTGGTGCCATTACTGGCGAAAATGATAAGAAGAA
GATCAAGGGAACTGTTGTGTTGATGAAGAAGAATGTGTTGGATTTTAATG
ACTTCAATGCATCGGTTCTGGACCGGGTTCATGAGCTGTTGGGACAGGGA
GTCCCTCTGCAGCTCGTCAGTGCTGTTCATGGTGATCCTGGTGAGTTTTT
TATTTTATTTTATTTTTTTATTTTTTTTCATGTTTTTGATGATGGGGTTA
TTGAAGTTGGGGGAGAGGAGAATGATGCCGTTTTGTGAGGGGTGAGATGG
GTTTTGAGTTTTGATGATGGGAGTTGGAAGAAGATGTGTTTTTTGGAAGA
GGTCAAGAGGGGTTATTCTCAGAAATTGAGTCAATGAGTTTCTTGACATC
TTCCATTCAACTGGGCACTTTTCTAAGTGCTTTTGTTTTTTGTGTTTTGT
GTTTTTTGTTTTGATGCTTTTGTAGCAAATGGGTTACAGGGGAAAATTGG
AAAACCAGCATACTTGGAAGACTGGATTACCACAATAACTTCTTTAACCG
CGGGCGAGTCTGCATTCAAGGTCACGTTCGACTGGGATGAGGAGATTGGA
GAGCCAGGGGCATTCATAATTAGAAACAATCACCACAGTGAGTTTTACCT
CAGGACTCTCACTCTTGAAGATGTTCCTGGACGTGGCAGAATTCACTTTG
TTTGTAATTCCTGGGTCTACCCTGCTCAGCACTACAAAACTGACCGTGTT
TTCTTCACTAATCAGGTAAGACTAATTTACTTGATACTAGGAGAGTCTGC
TGTGGCATTGTGGCTCATTGAGCTTAGGCAAGGAGAATTGTCTGCTAAAG
GAATGTGTTTATTTTATCTGCTGCAGACATATCTTCCAAGTGAAACACCA
GGGCCACTGCGCAAGTACAGAGAAGGGGAACTGGTGAATCTGAGGGGAGA
TGGAACCGGAGAGCTTAAGGAATGGGATCGAGTGTATGACTATGCTTACT
ATAATGATTTGGGGAATCCAGACAGGGATCTCAAATACGCCCGCCCTGTG
TGGGAGGATCTGCAGAGTATCCTTATCCCAGGAGGGGAAGAACTGGTAG
ACCACCATCTGAAAAAGGTAGATATTTGATGCAAAAATTCATATTGTTTT
CTCATGCTTTTATCATAAAAGGATGAATATGATTGATTTCTGCTCTTCTT
TTAATTAACAGATCCCAACACCGAGAGCAGATTGCCACTTGTGATGAGCT
TAAACATATATGTTCCAAGAGATGAAAGATTTGGTCACCTGAAGATGTCA
GACTTCCTGGCTTATGCCCTGAAATCCATAGTTCAATTCCTTCTCCCTGA
GTTTGAGGCTCTATGTGACATCACCCACAATGAGTTTGACAGCTTCCAAG
```

ATGTATTAGACCTCTACGAAGGAGGAATCAAGGTCCCAGAGGGCCCTTTA
CTGGACAAAATTAAGGACAACATCCCTCTTGAGATGCTCAAGGAACTTGT
TCGTACTGATGGGGAACATCTCTTCAAGTTCCCAATGCCCCAAGTCATCA
AAGGTACTGCATACATCTAACATCTTGTAATCTTTGAAGCCAGATTTATA
TATTTATTTTTCGTAAAATTGATGACGTTTTTATCATGCTGGAGCAGAGG
ATAAGTCTGCATGGAGGACCGATGAAGAATTTGCAAGAGAAATGCTGGCT
GGACTCAACCCAGTTGTCATCCGTCTACTCCAAGTAAACTACAGCTTCCT
TTCAAATATTTTTAAATGCCCTGTTTGTTTTCTGAGAAAATGGAACTTGG
AAAGGCTTCCAGACTTTGTTTTCTTTCCCTCCATCTACTGTTCTAGCTCT
TTTCTGATAATTATTGGCTTTTTCTACTTTGTTTGCAGGAGTTTCCTCCA
AAAAGCAAGCTGGATCCTGAAGTTTATGGCAACCAAAACAGTTCAATAAC
CAAAGAACACATAGAGAATCACCTGGATGACCTTACTATAAACGAGGTAA
CGCTCTTAGGTTCCCTTCTTTCAGACTAAATTTTTCAATGTCGACATGTT
AATTTTTTGCATTGGAACACAAGCCATAGTAACTGAAAAATGGTGCTTTT
TACTAGGCAATGGAGAAGAAGAGGCTATTCATATTAGATCACCATGATGT
TTTCATGCCATACCTGAGGAGGATAAACACAACTTCCACGAAAACTTATG
CCTCAAGGACTCTCCTCTTCCTGAAAGACGACGGAACTTTGAAGCCACTG
GCGATTGAATTGAGCCTACCACATCCTAGTGGGGATAAATTTGGAGCTGT
CAACAAAGTATATACGCCAGCTGAAAATGGTGTTGAAGGTTCCATTTGGC
AGCTGGCTAAAGCTTATGCTGCTGTGAATGACTCTGGCTATCATCAGCTC
CTCAGCCACTGGTATGTAATATCCCAAAGGAAAGTGAATACAGTTTGGGCT
TAAATCTGAAGCGGGTTGTGAATATCTTTGATGTTGGTTGCAGGTTGAATA
CACATGCTGCAATTGAGCCATTTGTGATTGCAACCAACAGGCAGCTCAGCG
TGCTTCATCCAATTCACAAGCTTTTGCATCCTCACTTCCGTGATACAATGA
ATATAAATGCATTAGCTCGACAAATCCTCATCAATGCTGGTGGAGTGGTGG
AGAGCACAGTTTTTCCATCAAAGTATGCCATGGAAATGTCATCTGTTGTTT
ACAAAGACTGGGTTCTTACTGAGCAAGCACTTCCTGCTGATCTCATCAAGA
GGTATATAAATACTGTTAGTGATTGTTTTCTTTCCTGCTGTGGAATGAATC
TAGTGAAAATTGTGATTTTCATCTAACTGATATGCTGCAACTTGGGCACTC
TTTCAGAGGAATGGCGGTTGAGGATTCAGAGGCTCCTCATGGACTCCGCCT
ACTGATAGATGACTACCCCTATGCTGTTGATGGACTTGAGATCTGGTCAGC

TATTGAGACATGGGTGAAAGAGTATTGCTCATTCTACTACAAGACAGATGA
GATGGTCCAGAAAGACTCTGAGCTTCAGTCCTGGTGGAAGGAAGTCAGGGA
AGAGGGTCATGGCGACAAGAAGGACGAGCCCTGGTGGCCTAAAATGCATAC
TGTCAAAGAGCTGATAGAAACATGCACCATTATCATCTGGGTGGCTTCTGC
TCTCCATGCTGCAGTGAATTTCGGGCAGTACCCTTATGCAGGCTACCTCCC
AAACCGCCCAACGATAAGCCGCAGATTCATGCCTGAAGAAGGCACTCCTGA
GTATGAAGAACTCAAGTCCAATCCTGATAAGGCTTTCCTGAAAACAATCAC
TGCCCAGCTGCAGACCCTTCTTGGCATCTCCCTTATTGAGGTCCTTTCCAG
GCATTCTTCCGATGAGGTTTATCTTGGACAGAGAGACACTCCTGAATGGAC
CCTGGACACAACACCATTGAAAGCTTTTGAGAAATTCGGAAGGAAGCTGGC
AGACATTGAAGAAATGATCATAGATAGAAATGGAAATGAGAGATTCAAGAA
CAGAGTTGGGCCTGTGAAGATACCATACACACTGCTCTACCCCACAAGCGA
AGGTGGGCTTACTGGCAAAGGGATTCCCAACAGTGTCTCCATCTAAATTTT
CCTGGAAAATCATGAGCACACTGCTGATCAAGATGGCTTAAATGCACATTG
CTAATATAGTATACTGTAATTTATAATACCTATTTTTCGACTTTGTAGGAT
TCATATTGATGCATATATTTATAATAAGGAATTATTTATTGCTAGAAAATT
GGGAGCTTTTCACTTTTTTTATGATCTGTGCCACACTTAATGTTAAAAGAT
GAAGGTGAAGTAGCAAAACAGTTGATCTGAATGCGCAGCCATTGATATCAG
GAATCAAAGTCAGATGGTGCAAATGCTCTCAAAACATCCACCCTCCCACAA
AATTATCTATAATTTACATGTTAACAAGAACTCAAGAGTGAGTAAGAAACT
ATGTTGAGAAATACTTTCTGAAACCACTGAGGAAAGTGTCCATTTGAAGAA
GTGTGAGACTCTTACCTAAGAAGTGTCTGTAGATTTGAATAGTAACTGCCA
ATATCTCTATCAAATCTTTATTATTACATGTATTAGATTTTGATATGATGC
TTGGATAGTATGCCTATAAACAAATGCATCCCCGAGCTTCTTCTTTGTATA
TTCTTCTGCTCTCACATTCTTGGCTTTCTTCTGCTTAGCTTTGTTGTTGTT
G

Numerous modification and variations in the practice of the invention are expected to occur to those skilled in the art upon consideration of the presently preferred embodiments thereof.

What is claimed is:

1. A purified polynucleotide encoding a *Vitus vinifera* lipoxygenase (LOX) polypeptide selected from the group consisting of:
   a) a polynucleotide comprising the sequence as set forth in SEQ ID NO: 2 or SEQ ID NO: 4,
   b) a DNA characterized by having at least 90% sequence identity to the sequence as set forth in SEQ ID NO: 2 or SEQ ID NO: 4 and which encodes a polypeptide having lipoxygenase enzyme activity; and
   c) a polynucleotide encoding the amino acid sequence as set forth in SEQ ID NO: 1 or SEQ ID NO: 3.

2. The polyriucleotide of claim 1 which is a DNA molecule.

3. The polynucleotide of claim 2 which is a cDNA molecule.

4. The DNA of claim 3 which is a wholly or partially chemically synthesized DNA molecule.

5. An anti-sense polynucleotide which specifically hybridizes with the polynucleotide of SEQ ID NO: 2 or 4.

6. The polynucleotide of claim 1 operably linked to a heterologous promoter.

7. An expression construct comprising the polynucleotide of claim 1.

8. A host cell transformed or transfected with the expression construct according to claim 7.

9. A host cell comprising the polynucleotide of claim 6.

10. The host cell of claim 9 which is a *Vitis vinifera* cell.

11. The host cell of claim 10 which is a microorganism selected from the group consisting of yeast and bacteria.

12. A transformed plant comprising the host cell of claim 8.

13. The transformed plant of claim 12 wherein the expression construct comprises a polynucleotide encoding the *Vitis vinifera* LOX polypeptide operably linked to a heterologous promoter.

14. The transformed plant of claim 12 which is *Vitis vinifera*.

15. A method of producing a *Vitis vinifera* LOX polypeptide comprising the step of culturing a host cell transformed with the polynucleotide of claim 1 under conditions selected to express the LOX polypeptide and isolating said LOX polypeptide.

* * * * *

UNITED STATES PATENT AND TRADEMARK OFFICE
CERTIFICATE OF CORRECTION

PATENT NO.    : 6,787,684 B2
DATED         : September 7, 2004
INVENTOR(S)   : Richard A. Descenzo et al.

It is certified that error appears in the above-identified patent and that said Letters Patent is hereby corrected as shown below:

<u>Column 63,</u>
Line 47, after "2. The," please delete "polyriucleotide" and insert -- polynucleotide -- in its place.

Signed and Sealed this

First Day of February, 2005

JON W. DUDAS
*Director of the United States Patent and Trademark Office*

SEQUENCE LISTING

<160> NUMBER OF SEQ ID NOS: 45

<210> SEQ ID NO 1
<211> LENGTH: 862
<212> TYPE: PRT
<213> ORGANISM: Vitis LOX 1

<400> SEQUENCE: 1

Met Lys Lys Lys Leu Leu Ser Ile Val Ser Ala Ile Thr Gly Glu Asn

-continued

```
1               5                   10                  15
Asp Lys Lys Lys Ile Glu Gly Thr Ile Val Leu Met Lys Lys Asn Val
                20                  25                  30
Leu Asp Phe Asn Asp Phe Asn Ala Pro Val Arg Asp Arg Val His Glu
                35                  40                  45
Leu Phe Gly Gln Gly Val Ser Leu Gln Leu Val Ser Ala Val His Gly
                50                  55                  60
Asp Pro Ala Asn Gly Leu Gln Gly Lys Leu Gly Lys Pro Ala Tyr Leu
65                  70                  75                  80
Glu Asp Trp Ile Thr Thr Ile Thr Ser Leu Thr Ala Gly Glu Ser Ala
                85                  90                  95
Phe Lys Val Thr Phe Asp Trp Asp Glu Glu Ile Gly Glu Pro Gly Ala
                100                 105                 110
Phe Ile Ile Arg Asn Asn His His Ser Glu Phe Tyr Leu Arg Thr Leu
                115                 120                 125
Thr Leu Glu Asp Val Pro Gly Arg Gly Arg Ile His Phe Val Cys Asn
                130                 135                 140
Ser Trp Val Tyr Pro Ala Lys His Tyr Lys Thr Asp Arg Val Phe Phe
145                 150                 155                 160
Thr Asn Gln Thr Tyr Leu Pro Ser Glu Thr Pro Gly Pro Leu Arg Lys
                165                 170                 175
Tyr Arg Lys Gly Glu Leu Val Asn Leu Arg Gly Asp Gly Thr Gly Glu
                180                 185                 190
Leu Lys Glu Trp Asp Arg Val Tyr Asp Tyr Ala Tyr Tyr Asn Asp Leu
                195                 200                 205
Gly Lys Pro Asp Arg Asp Leu Lys Tyr Ala Arg Pro Val Leu Gly Gly
                210                 215                 220
Ser Ala Glu Tyr Pro Tyr Pro Arg Arg Gly Arg Thr Gly Arg Pro Pro
225                 230                 235                 240
Ser Glu Lys Asp Pro Lys Thr Glu Ser Arg Leu Pro Leu Val Met Ser
                245                 250                 255
Leu Asn Ile Tyr Val Pro Arg Asp Glu Arg Phe Gly His Leu Lys Met
                260                 265                 270
Ser Asp Phe Leu Ala Tyr Ala Leu Lys Ser Ile Val Gln Phe Leu Leu
                275                 280                 285
Pro Glu Phe Glu Ala Leu Cys Asp Ile Thr Pro Asn Glu Phe Asp Ser
                290                 295                 300
Phe Gln Asp Val Leu Asp Leu Tyr Glu Gly Gly Ile Lys Val Pro Glu
305                 310                 315                 320
Gly Pro Leu Leu Asp Lys Ile Lys Asp Asn Ile Pro Leu Glu Met Leu
                325                 330                 335
Lys Glu Leu Val Arg Thr Asp Gly Glu His Leu Phe Lys Phe Pro Met
                340                 345                 350
Pro Gln Val Ile Lys Glu Asp Lys Ser Ala Trp Arg Thr Asp Glu Glu
                355                 360                 365
Phe Ala Arg Glu Met Leu Ala Gly Leu Asn Pro Val Val Ile Arg Leu
                370                 375                 380
Leu Gln Glu Phe Pro Pro Lys Ser Lys Leu Asp Pro Glu Val Tyr Gly
385                 390                 395                 400
Asn Gln Asn Ser Ser Ile Thr Lys Glu His Ile Glu Asn His Leu Asp
                405                 410                 415
Asp Leu Thr Ile Asn Glu Ala Met Glu Lys Lys Arg Leu Phe Ile Leu
                420                 425                 430
```

-continued

```
Asp His His Asp Val Phe Met Pro Tyr Leu Arg Arg Ile Asn Thr Thr
        435                 440                 445

Ser Thr Lys Thr Tyr Ala Ser Arg Thr Leu Leu Phe Leu Lys Asp Asp
    450                 455                 460

Gly Thr Leu Lys Pro Leu Ala Ile Glu Leu Ser Leu Pro His Pro Asn
465                 470                 475                 480

Gly Asp Lys Phe Gly Ala Val Asn Lys Val Tyr Thr Pro Ala Glu Asp
                485                 490                 495

Gly Val Glu Gly Ser Ile Trp Gln Leu Ala Lys Ala Tyr Ala Ala Val
            500                 505                 510

Asn Asp Ser Gly Tyr His Gln Leu Leu Ser His Trp Leu Asn Thr His
        515                 520                 525

Ala Ala Ile Glu Pro Phe Val Ile Ala Thr Asn Arg Gln Leu Ser Val
    530                 535                 540

Leu His Pro Ile His Lys Leu Leu His Pro His Phe Arg Asp Thr Met
545                 550                 555                 560

Asn Ile Asn Ala Leu Ala Arg Gln Ile Leu Ile Asn Ala Gly Gly Val
                565                 570                 575

Val Glu Ser Thr Val Phe Pro Ser Lys Tyr Ala Met Glu Met Ser Ser
            580                 585                 590

Val Val Tyr Lys Asp Trp Val Leu Thr Glu Gln Ala Leu Pro Ala Asp
        595                 600                 605

Leu Ile Lys Arg Gly Met Ala Val Glu Asp Ser Glu Ala Pro His Gly
    610                 615                 620

Leu Arg Leu Leu Ile Asp Asp Tyr Pro Tyr Ala Val Asp Gly Leu Glu
625                 630                 635                 640

Ile Trp Ser Ala Ile Glu Thr Trp Val Lys Glu Tyr Cys Ser Phe Tyr
                645                 650                 655

Tyr Lys Thr Asp Glu Met Val Gln Lys Asp Ser Glu Leu Gln Ser Trp
            660                 665                 670

Trp Lys Glu Val Arg Glu Glu Gly His Gly Asp Lys Lys Asp Glu Pro
        675                 680                 685

Trp Trp Pro Lys Met Arg Thr Val Lys Glu Leu Ile Glu Thr Cys Thr
    690                 695                 700

Ile Ile Ile Trp Val Ala Ser Ala Leu His Ala Ala Val Asn Phe Gly
705                 710                 715                 720

Gln Tyr Pro Tyr Ala Gly Tyr Leu Pro Asn Arg Pro Thr Ile Ser Arg
                725                 730                 735

Arg Phe Met Pro Glu Glu Gly Thr Pro Glu Tyr Glu Glu Leu Lys Ser
            740                 745                 750

Asn Pro Asp Lys Ala Phe Leu Lys Thr Ile Thr Ala Gln Leu Gln Thr
        755                 760                 765

Leu Leu Gly Ile Ser Leu Ile Glu Val Leu Ser Arg His Ser Ser Asp
    770                 775                 780

Glu Val Tyr Leu Gly Gln Arg Asp Thr Pro Glu Trp Thr Leu Asp Thr
785                 790                 795                 800

Thr Pro Leu Lys Ala Phe Glu Lys Phe Gly Arg Lys Leu Ala Asp Ile
                805                 810                 815

Glu Glu Met Ile Ile Asp Arg Asn Gly Asn Glu Arg Phe Lys Asn Arg
            820                 825                 830

Val Gly Pro Val Lys Ile Pro Tyr Thr Leu Leu Tyr Pro Thr Ser Glu
        835                 840                 845
```

-continued

Gly Gly Leu Thr Gly Lys Gly Ile Pro Asn Ser Val Ser Ile
     850             855             860

<210> SEQ ID NO 2
<211> LENGTH: 4687
<212> TYPE: DNA
<213> ORGANISM: Vitis LOX 1

<400> SEQUENCE: 2

| | |
|---|---|
| atgaagaaga agcttctttc aattgttagt gccatcactg gggaaaatga taagaagaag | 60 |
| atcgagggaa ctattgtgtt gatgaagaag aatgtgttgg attttaatga cttcaatgca | 120 |
| ccggttcggg accgggttca tgagcttttt ggacagggag tctctctgca gctcgtcagt | 180 |
| gctgttcatg gtgatcctgg tgagtttttt ttttttttt tttccttcat gttttttgatg | 240 |
| atgggggttgt tgaagttgga ggagaggagg ttgataccgt tttgtgaggg tgagatgggt | 300 |
| tctgaattt gatgatagca attggaaaaa gatgtgattt ttggaagagg ccaagagggg | 360 |
| ttgttattct cagagatgag tcaaatgact ttcttgacat cttccattca actgggcact | 420 |
| tttctaactg cttttgtttt tgtgttttg ttttaatgc ttttgttttc tacttctttc | 480 |
| tcttgtttat atttcttttc atcaaccact atacatgccc acctaactca atatgaaatt | 540 |
| cccatgcagc tgcccttttt tttaagccac tagatcttgg gtgattttt agtcttagat | 600 |
| cttgggttag atttccccag atttcacaaa agttgaaact gaaattcata aaatttttga | 660 |
| ggatcactcc tgttggagtt aaagagaaag aattgccata aaccaaggag atgaattgtt | 720 |
| gtgaaatatt tctcaaaact tcatcatcaa atacctgcca aaacagccac agtttctgaa | 780 |
| atttcatgca gcaaagccac tgctgcttgt agcaagtcca agctcaaaca taaaagcctt | 840 |
| ttcaacccag tgatttttga gaataacatg taaaaatgca gtgaccatct gttagtgatg | 900 |
| atattgaact tgtgtgcctt ttgtagcaaa tgggttacag gggaaacttg ggaaaccagc | 960 |
| atacttggaa gactggatta ccacaattac ttcttaacc gctggcgagt ctgcattcaa | 1020 |
| ggtcacgttc gactgggatg aggagattgg agagccaggg gcattcataa ttagaaacaa | 1080 |
| tcaccacagt gagttttacc tcaggactct cactcttgaa gatgttcctg acgtggcag | 1140 |
| aattcacttt gtttgtaatt cctgggtcta ccctgctaag cactacaaaa ctgaccgtgt | 1200 |
| tttcttcact aatcaggtaa gactaatttg cttgatacta ggagagtctg ctgtggcatt | 1260 |
| gtggcccatt gagcttaggc aaggagaatt gtctgctaaa ggaatgtgtt tatttatct | 1320 |
| gctgcagaca tatcttccaa gtgaaacacc agggccactg cgcaagtaca gaaaagggga | 1380 |
| actggtgaat ctgaggggag atggaaccgg agagcttaag gaatgggatc gagtgtatga | 1440 |
| ctatgcttac tataatgatt tggggaagcc agacagggat ctcaaatatg cccgccctgt | 1500 |
| gctgggagga tctgcagagt atccttatcc caggagggga agaactggta gaccaccatc | 1560 |
| tgaaaaaggt agatatttga tacacaaatt catattgttt ctcatgcttt tatcataaaa | 1620 |
| ggatgaatat gattgatttc tgctcttctt ttaattaaca gatcccaaaa ctgagagcag | 1680 |
| attgccactt gtgatgagct taaacatata tgttccaaga gatgaacgat ttggtcacct | 1740 |
| gaagatgtca gacttcctgg cttatgccct gaaatccata gttcaattcc ttctccctga | 1800 |
| gtttgaggct ctatgtgaca tcaccccaa tgagtttgac agcttccaag atgtattaga | 1860 |
| cctctacgaa ggaggaatca aggtcccaga gggccctta ctggacaaaa ttaaggacaa | 1920 |
| catccctctt gagatgctca aggaacttgt tcgtaccgat ggggaacatc tcttcaagtt | 1980 |
| cccaatgccc caagtcatca aggtactgc atacatctaa catcttgtaa tctttgaagc | 2040 |

```
cagatttata tatttatttt tcataaaatt gatgacgttt ttatcatgct ggagcagagg    2100
ataagtctgc atggaggact gacgaagaat ttgctagaga aatgctggct ggactcaacc    2160
cagttgtcat ccgtctactc caagtaaact acagcttcct ttcaaataat ttttaatgcc    2220
ctgtttgttt tctgagaaaa tggaacttgg aaaggcttcc agactttgtt ttctttccct    2280
ccatctactg ttctagctct tttctgataa ttattggctc tttctacttt gtttgaagga    2340
gtttcctcca aaaagcaagc tggatcctga agtttatggc aaccaaaaca gttcaataac    2400
caaagaacac atagagaatc acctggatga ccttactata aacgaggtaa cgctcttagg    2460
ttccgttctt tcaaactaaa tttttcaatg tcgacatgtt aattttttgc attggaacac    2520
aagccatagt aactgaaaaa tggtgctttt tactaggcaa tggagaagaa gaggctattc    2580
atattagatc accatgatgt tttcatgcca tacctgagga ggataaacac aacttccacg    2640
aaaacttacg cctcaaggac tctcctcttc ctgaaagacg acggaacttt gaagccactg    2700
gcgattgaat tgagcctacc acatcctaat ggggataaat tcggagctgt caacaaagta    2760
tacacaccag ctgaagatgg cgttgaaggt tccatttggc agctggctaa agcttatgct    2820
gctgtgaatg actctggcta tcatcagctc ctcagccact ggtacgtaat ctcccaaagg    2880
aaagtgcgta cagttggggc gtaaatctga agcgggttat gaatatcttt gatgttggtt    2940
gcaggttgaa tacacatgct gcaattgagc catttgtgat tgcaaccaac aggcagctca    3000
gtgtgcttca cccaattcac aagcttttgc atcctcactt ccgtgatacg atgaatataa    3060
atgcattagc tcgacaaatc ctcatcaatg ctggtggagt ggtggagagc acagtttttc    3120
catcaaagta tgccatggaa atgtcatctg ttgtttacaa agactgggtt ctcactgagc    3180
aagcacttcc tgctgatctc atcaagaggt atataaatac tgttagtgat tgttttcttt    3240
cctgctgtgc aatgaatcta gtgaaaattg tgattttcat ctaactgata tgctccaact    3300
tgggcactct ttcagaggaa tggcggttga ggattcagag gcccctcatg gactccgcct    3360
actgatagat gactacccct atgctgttga tggacttgag atctggtcag ctattgagac    3420
atgggtgaaa gagtattgct cattctacta caagacagat gagatggtcc agaaagactc    3480
tgagcttcag tcctggtgga aggaagtcag ggaagagggt catggcgaca agaaggacga    3540
gccttggtgg cctaaaatgc gtactgtcaa agagctgata gaaacatgca ccattatcat    3600
ctgggtggct tctgctctcc atgctgcagt gaatttcggg cagtacccct tatgcaggcta    3660 cctcccaaac cgcccaacga taagccgcag attcatgcct gaagaaggca ctcctgagta    3720
tgaagaactc aagtccaatc ctgataaggc tttcctgaaa acaatcactg cccagctgca    3780
gacccttctt ggcatctccc ttattgaggt cctttccagg cattcttccg atgaggttta    3840
tcttggacag agagacactc ctgaatggac cctggcacaa acaccattga aagcttttga    3900
gaaattcgga aggaagctgg cagacattga agaaatgatc atagatagaa atggaaatga    3960
gagattcaag aacagagttg ggcctgtgaa gataccatac acactgctct accccacaag    4020
cgaaggtggg cttactggca aagggattcc caacagtgtc tccatctaaa ttttcctgga    4080
aaatcatgag cacactgctg atcaagatgg cttaaatgca cattgctaat atagtatact    4140
gtaatttata atacctattt ttcgactttg taggattcat attgatgcat atatttataa    4200
taaggaatta tttattgcta gaaaattggg agcttttcac tttttttatg atctgtgcca    4260
cacttaatgt taaagatgaa aggtgaagta gcaaaacagt tgatctgaat gcgcagccat    4320
tgatatcagg aatcaaagtc agatggtgca aatgctctca aaacatccac cctcccacaa    4380
aattatctat aatttacatg ttaacaagaa ctcaagagtg agtaagaaac tatgttgaga    4440
```

-continued

```
aatactttct gaaaccactg aggaaagtgt ccatttgaag aagtgtgaga ctcttaccta   4500
agaagtgtct gtagatttga atagtaactg ccaatatctc tatcaaatct ttattattac   4560
atgtattaga ttttgatatg atgcttggat agtatgccta taaacaaatg catccccgag   4620
cttcttcttt gtatattctt ctgctctcac attcttggct ttcttctgct tagctttgtt   4680
gttgttg                                                             4687
```

<210> SEQ ID NO 3
<211> LENGTH: 859
<212> TYPE: PRT
<213> ORGANISM: Vitis LOX 2

<400> SEQUENCE: 3

```
Met Ile His Ser Ile Val Gly Ala Ile Thr Gly Glu Asn Asp Lys Lys
1               5                   10                  15

Lys Ile Lys Gly Thr Val Val Leu Met Lys Lys Asn Val Leu Asp Phe
            20                  25                  30

Asn Asp Phe Asn Ala Ser Val Leu Asp Arg Val His Glu Leu Leu Gly
        35                  40                  45

Gln Gly Val Pro Leu Gln Leu Val Ser Ala Val His Gly Asp Pro Ala
    50                  55                  60

Asn Gly Leu Gln Gly Lys Ile Gly Lys Pro Ala Tyr Leu Glu Asp Trp
65                  70                  75                  80

Ile Thr Thr Ile Thr Ser Leu Thr Ala Gly Glu Ser Ala Phe Lys Val
                85                  90                  95

Thr Phe Asp Trp Asp Glu Glu Ile Gly Glu Pro Gly Ala Phe Ile Ile
            100                 105                 110

Arg Asn Asn His His Ser Glu Phe Tyr Leu Arg Thr Leu Thr Leu Glu
        115                 120                 125

Asp Val Pro Gly Arg Gly Arg Ile His Phe Val Cys Asn Ser Trp Val
    130                 135                 140

Tyr Pro Ala Gln His Tyr Lys Thr Asp Arg Val Phe Phe Thr Asn Gln
145                 150                 155                 160

Thr Tyr Leu Pro Ser Glu Thr Pro Gly Pro Leu Arg Lys Tyr Arg Glu
                165                 170                 175

Gly Glu Leu Val Asn Leu Arg Gly Asp Gly Thr Gly Glu Leu Lys Glu
            180                 185                 190

Trp Asp Arg Val Tyr Asp Tyr Ala Tyr Tyr Asn Asp Leu Gly Asn Pro
        195                 200                 205

Asp Arg Asp Leu Lys Tyr Ala Arg Pro Val Leu Gly Gly Ser Ala Glu
    210                 215                 220

Tyr Pro Tyr Pro Arg Arg Gly Arg Thr Gly Arg Pro Pro Ser Glu Lys
225                 230                 235                 240

Asp Pro Asn Thr Glu Ser Arg Leu Pro Leu Val Met Ser Leu Asn Ile
                245                 250                 255

Tyr Val Pro Arg Asp Glu Arg Phe Gly His Leu Lys Met Ser Asp Phe
            260                 265                 270

Leu Ala Tyr Ala Leu Lys Ser Ile Val Gln Phe Leu Leu Pro Glu Phe
        275                 280                 285

Glu Ala Leu Cys Asp Ile Thr His Asn Glu Phe Asp Ser Phe Gln Asp
    290                 295                 300

Val Leu Asp Leu Tyr Glu Gly Gly Ile Lys Val Pro Glu Gly Pro Leu
305                 310                 315                 320
```

-continued

Leu Asp Lys Ile Lys Asp Asn Ile Pro Leu Glu Met Leu Lys Glu Leu
            325                 330                 335

Val Arg Thr Asp Gly Glu His Leu Phe Lys Phe Pro Met Pro Gln Val
            340                 345                 350

Ile Lys Glu Asp Lys Ser Ala Trp Arg Thr Asp Glu Glu Phe Ala Arg
            355                 360                 365

Glu Met Leu Ala Gly Leu Asn Pro Val Val Ile Arg Leu Leu Gln Glu
    370                 375                 380

Phe Pro Pro Lys Ser Lys Leu Asp Pro Glu Val Tyr Gly Asn Gln Asn
385                 390                 395                 400

Ser Ser Ile Thr Lys Glu His Ile Glu Asn His Leu Asp Asp Leu Thr
                405                 410                 415

Ile Asn Glu Ala Met Glu Lys Lys Arg Leu Phe Ile Leu Asp His His
            420                 425                 430

Asp Val Phe Met Pro Tyr Leu Arg Arg Ile Asn Thr Thr Ser Thr Lys
            435                 440                 445

Thr Tyr Ala Ser Arg Thr Leu Leu Phe Leu Lys Asp Asp Gly Thr Leu
    450                 455                 460

Lys Pro Leu Ala Ile Glu Leu Ser Leu Pro His Pro Ser Gly Asp Lys
465                 470                 475                 480

Phe Gly Ala Val Asn Lys Val Tyr Thr Pro Ala Glu Asn Gly Val Glu
                485                 490                 495

Gly Ser Ile Trp Gln Leu Ala Lys Ala Tyr Ala Ala Val Asn Asp Ser
            500                 505                 510

Gly Tyr His Gln Leu Leu Ser His Trp Leu Asn Thr His Ala Ala Ile
        515                 520                 525

Glu Pro Phe Val Ile Ala Thr Asn Arg Gln Leu Ser Val Leu His Pro
    530                 535                 540

Ile His Lys Leu Leu His Pro His Phe Arg Asp Thr Met Asn Ile Asn
545                 550                 555                 560

Ala Leu Ala Arg Gln Ile Leu Ile Asn Ala Gly Gly Val Val Glu Ser
                565                 570                 575

Thr Val Phe Pro Ser Lys Tyr Ala Met Glu Met Ser Ser Val Val Tyr
            580                 585                 590

Lys Asp Trp Val Leu Thr Glu Gln Ala Leu Pro Ala Asp Leu Ile Lys
        595                 600                 605

Arg Gly Met Ala Val Glu Asp Ser Glu Ala Pro His Gly Leu Arg Leu
    610                 615                 620

Leu Ile Asp Asp Tyr Pro Tyr Ala Val Asp Gly Leu Glu Ile Trp Ser
625                 630                 635                 640

Ala Ile Glu Thr Trp Val Lys Glu Tyr Cys Ser Phe Tyr Tyr Lys Thr
                645                 650                 655

Asp Glu Met Val Gln Lys Asp Ser Glu Leu Gln Ser Trp Trp Lys Glu
            660                 665                 670

Val Arg Glu Glu Gly His Gly Asp Lys Lys Asp Glu Pro Trp Trp Pro
        675                 680                 685

Lys Met His Thr Val Lys Glu Leu Ile Glu Thr Cys Thr Ile Ile Ile
    690                 695                 700

Trp Val Ala Ser Ala Leu His Ala Ala Val Asn Phe Gly Gln Tyr Pro
705                 710                 715                 720

Tyr Ala Gly Tyr Leu Pro Asn Arg Pro Thr Ile Ser Arg Arg Phe Met
                725                 730                 735

Pro Glu Glu Gly Thr Pro Glu Tyr Glu Glu Leu Lys Ser Asn Pro Asp

```
                  740                745                750
Lys Ala Phe Leu Lys Thr Ile Thr Ala Gln Leu Gln Thr Leu Leu Gly
                755                760                765
Ile Ser Leu Ile Glu Val Leu Ser Arg His Ser Ser Asp Glu Val Tyr
            770                775                780
Leu Gly Gln Arg Asp Thr Pro Glu Trp Thr Leu Asp Thr Thr Pro Leu
785                790                795                800
Lys Ala Phe Glu Lys Phe Gly Arg Lys Leu Ala Asp Ile Glu Glu Met
                805                810                815
Ile Ile Asp Arg Asn Gly Asn Glu Arg Phe Lys Asn Arg Val Gly Pro
                820                825                830
Val Lys Ile Pro Tyr Thr Leu Leu Tyr Pro Thr Ser Glu Gly Gly Leu
            835                840                845
Thr Gly Lys Gly Ile Pro Asn Ser Val Ser Ile
850                855

<210> SEQ ID NO 4
<211> LENGTH: 4237
<212> TYPE: DNA
<213> ORGANISM: Vitis LOX sequence 2

<400> SEQUENCE: 4
atgattcatt caattgttgg tgccattact ggcgaaaatg ataagaagaa gatcaaggga      60
actgttgtgt tgatgaagaa gaatgtgttg gattttaatg acttcaatgc atcggttctg     120
gaccgggttc atgagctgtt gggacaggga gtccctctgc agctcgtcag tgctgttcat     180
ggtgatcctg gtgagttttt tattttattt tatttttttta ttttttttca tgttttttgat     240 gatggggtta ttgaagttgg gggagaggag aatgatgccg ttttgtgagg ggtgagatgg     300
gttttgagtt tgatgatgg gagttggaag aagatgtgtt ttttggaaga ggtcaagagg     360
ggttattctc agaaattgag tcaatgagtt tcttgacatc ttccattcaa ctgggcactt     420
ttctaagtgc ttttgttttt tgtgttttgt gttttttgtt ttgatgcttt tgtagcaaat     480
gggttacagg ggaaaattgg aaaaccagca tacttggaag actggattac acaataact     540 tctttaaccg cgggcgagtc tgcattcaag gtcacgttcg actgggatga ggagattgga     600
gagccagggg cattcataat tagaaacaat caccacagtg agttttacct caggactctc     660
actcttgaag atgttcctgg acgtggcaga attcactttg tttgtaattc ctgggtctac     720
cctgctcagc actacaaaac tgaccgtgtt ttcttcacta atcaggtaag actaatttac     780
ttgatactag gagagtctgc tgtggcattg tggctcattg agcttaggca aggagaattg     840
tctgctaaag gaatgtgttt attttatctg ctgcagacat atcttccaag tgaaacacca     900
gggccactgc gcaagtacag agaaggggaa ctggtgaatc tgaggggaga tggaaccgga     960
gagcttaagg aatgggatcg agtgtatgac tatgcttact ataatgattt ggggaatcca    1020
gacagggatc tcaaatacgc ccgccctgtg ctgggaggat ctgcagagta tccttatccc    1080
aggaggggaa gaactggtag accaccatct gaaaaggta gatatttgat gcaaaaattc    1140
atattgtttt ctcatgcttt tatcataaaa ggatgaatat gattgatttc tgctcttctt    1200
ttaattaaca gatcccaaca ccgagagcag attgccactt gtgatgagct taaacatata    1260
tgttccaaga gatgaaagat ttggtcacct gaagatgtca gacttcctgg cttatgccct    1320
gaaatccata gttcaattcc ttctccctga gtttgaggct ctatgtgaca tcacccacaa    1380
tgagtttgac agcttccaag atgtattaga cctctacgaa ggaggaatca aggtcccaga    1440
```

-continued

```
gggccccttta ctggacaaaa ttaaggacaa catccctctt gagatgctca aggaacttgt    1500
tcgtactgat ggggaacatc tcttcaagtt cccaatgccc caagtcatca aaggtactgc    1560
atacatctaa catcttgtaa tctttgaagc cagatttata tatttatttt tcgtaaaatt    1620
gatgacgttt ttatcatgct ggagcagagg ataagtctgc atggaggacc gatgaagaat    1680
ttgcaagaga aatgctggct ggactcaacc cagttgtcat ccgtctactc caagtaaact    1740
acagcttcct ttcaaatatt tttaaatgcc ctgtttgttt tctgagaaaa tggaacttgg    1800
aaaggcttcc agactttgtt ttctttccct ccatctactg ttctagctct tttctgataa    1860
ttattggctt tttctacttt gttttgcagga gtttcctcca aaaagcaagc tggatcctga    1920
agtttatggc aaccaaaaca gttcaataac caaagaacac atagagaatc acctggatga    1980
ccttactata aacgaggtaa cgctcttagg ttcccttctt tcagactaaa tttttcaatg    2040
tcgacatgtt aattttttgc attggaacac aagccatagt aactgaaaaa tggtgctttt    2100
tactaggcaa tggagaagaa gaggctattc atattagatc accatgatgt tttcatgcca    2160
tacctgagga ggataaacac aacttccacg aaaacttatg cctcaaggac tctcctcttc    2220
ctgaaagacg acggaacttt gaagccactg gcgattgaat tgagcctacc acatcctagt    2280
ggggataaat ttggagctgt caacaaagta tatacgccag ctgaaaatgg tgttgaaggt    2340
tccatttggc agctggctaa agcttatgct gctgtgaatg actctggcta tcatcagctc    2400
ctcagccact ggtatgtaat atcccaaagg aaagtgaata cagtttgggc ttaaatctga    2460
agcgggttgt gaatatcttt gatgttggtt gcaggttgaa tacacatgct gcaattgagc    2520
catttgtgat tgcaaccaac aggcagctca gcgtgcttca tccaattcac aagcttttgc    2580
atcctcactt ccgtgataca atgaatataa atgcattagc tcgacaaatc ctcatcaatg    2640
ctggtggagt ggtggagagc acagtttttc catcaaagta tgccatggaa atgtcatctg    2700
ttgtttacaa agactgggtt cttactgagc aagcacttcc tgctgatctc atcaagaggt    2760
atataaatac tgttagtgat tgttttcttt cctgctgtgg aatgaatcta gtgaaaattg    2820
tgattttcat ctaactgata tgctgcaact tgggcactct ttcagaggaa tggcggttga    2880
ggattcagag gctcctcatg gactccgcct actgatagat gactacccct atgctgttga    2940
tggacttgag atctggtcag ctattgagac atgggtgaaa gagtattgct cattctacta    3000
caagacagat gagatggtcc agaaagactc tgagcttcag tcctggtgga aggaagtcag    3060
ggaagagggt catggcgaca agaaggacga gccctggtgg cctaaaatgc atactgtcaa    3120
agagctgata gaaacatgca ccattatcat ctgggtggct tctgctctcc atgctgcagt    3180
gaatttcggg cagtacccctt atgcaggcta cctcccaaac cgcccaacga taagccgcag    3240
attcatgcct gaagaaggca ctcctgagta tgaagaactc aagtccaatc ctgataaggc    3300
tttcctgaaa acaatcactg cccagctgca gacccttctt ggcatctccc ttattgaggt    3360
cctttccagg cattcttccg atgaggttta tcttggacag agacactc ctgaatggac    3420 cctggacaca acaccattga aagcttttga gaaattcgga aggaagctgg cagacattga    3480
agaaatgatc atagatagaa atggaaatga gagattcaag aacagagttg ggcctgtgaa    3540
gataccatac acactgctct accccacaag cgaaggtggg cttactggca aagggattcc    3600
caacagtgtc tccatctaaa ttttcctgga aaatcatgag cacactgctg atcaagatgg    3660
cttaaatgca cattgctaat atagtatact gtaatttata atacctatttt ttcgactttg    3720 taggattcat attgatgcat atatttataa taaggaatta tttattgcta gaaaattggg    3780
agcttttcac ttttttttatg atctgtgcca cacttaatgt taaaagatga aggtgaagta    3840
```

```
gcaaaacagt tgatctgaat gcgcagccat tgatatcagg aatcaaagtc agatggtgca      3900
aatgctctca aaacatccac cctcccacaa aattatctat aatttacatg ttaacaagaa      3960
ctcaagagtg agtaagaaac tatgttgaga aatactttct gaaaccactg aggaaagtgt      4020
ccatttgaag aagtgtgaga ctcttaccta agaagtgtct gtagatttga atagtaactg      4080
ccaatatctc tatcaaatct ttattattac atgtattaga ttttgatatg atgcttggat      4140
agtatgccta taaacaaatg catccccgag cttcttcttt gtatattctt ctgctctcac      4200
attcttggct ttcttctgct tagctttgtt gttgttg                              4237

<210> SEQ ID NO 5
<211> LENGTH: 23
<212> TYPE: DNA
<213> ORGANISM: primer LOXDG697U
<220> FEATURE:
<221> NAME/KEY: misc_feature
<222> LOCATION: (3)..(3)
<223> OTHER INFORMATION: n= a or g or c or t
<221> NAME/KEY: misc_feature
<222> LOCATION: (6)..(6)
<223> OTHER INFORMATION: y=c or t
<221> NAME/KEY: misc_feature
<222> LOCATION: (10)..(10)
<223> OTHER INFORMATION: m=a or c
<221> NAME/KEY: misc_feature
<222> LOCATION: (13)..(13)
<223> OTHER INFORMATION: m=a or c
<221> NAME/KEY: misc_feature
<222> LOCATION: (19)..(19)
<223> OTHER INFORMATION: m=a or c
<221> NAME/KEY: misc_feature
<222> LOCATION: (9)..(9)
<223> OTHER INFORMATION: n= a or g or c or t
<221> NAME/KEY: misc_feature
<222> LOCATION: (12)..(12)
<223> OTHER INFORMATION: n= a or g or c or t
<221> NAME/KEY: misc_feature
<222> LOCATION: (15)..(15)
<223> OTHER INFORMATION: n= a or g or c or t
<221> NAME/KEY: misc_feature
<222> LOCATION: (18)..(18)
<223> OTHER INFORMATION: n= a or g or c or t
<221> NAME/KEY: misc_feature
<222> LOCATION: (21)..(21)
<223> OTHER INFORMATION: n= a or g or c or t

<400> SEQUENCE: 5
ccntayccnm gnmgnggnmg nac                                               23

<210> SEQ ID NO 6
<211> LENGTH: 23
<212> TYPE: DNA
<213> ORGANISM: primer LOXDG1081U
<220> FEATURE:
<221> NAME/KEY: misc_feature
<222> LOCATION: (3)..(3)
<223> OTHER INFORMATION: n= a or g or c or t
<221> NAME/KEY: misc_feature
<222> LOCATION: (18)..(18)
<223> OTHER INFORMATION: n= a or g or c or t
<221> NAME/KEY: misc_feature
<222> LOCATION: (21)..(21)
<223> OTHER INFORMATION: n= a or g or c or t
<221> NAME/KEY: misc_feature
<222> LOCATION: (6)..(6)
<223> OTHER INFORMATION: y= c or t
<221> NAME/KEY: misc_feature
<222> LOCATION: (15)..(15)
<223> OTHER INFORMATION: y= c or t
<221> NAME/KEY: misc_feature
<222> LOCATION: (9)..(9)
```

```
<223> OTHER INFORMATION: r= a or g
<221> NAME/KEY: misc_feature
<222> LOCATION: (12)..(12)
<223> OTHER INFORMATION: r= a or g
<221> NAME/KEY: misc_feature
<222> LOCATION: (19)..(19)
<223> OTHER INFORMATION: m= a or c

<400> SEQUENCE: 6
acngaygarg arttygcnmg nga                                         23

<210> SEQ ID NO 7
<211> LENGTH: 23
<212> TYPE: DNA
<213> ORGANISM: primer LOXDG1081L
<220> FEATURE:
<221> NAME/KEY: misc_feature
<222> LOCATION: (3)..(3)
<223> OTHER INFORMATION: n= a or g or c or t
<221> NAME/KEY: misc_feature
<222> LOCATION: (5)..(5)
<223> OTHER INFORMATION: k=g or t
<221> NAME/KEY: misc_feature
<222> LOCATION: (6)..(6)
<223> OTHER INFORMATION: n= a or g or c or t
<221> NAME/KEY: misc_feature
<222> LOCATION: (21)..(21)
<223> OTHER INFORMATION: n= a or g or c or t
<221> NAME/KEY: misc_feature
<222> LOCATION: (9)..(9)
<223> OTHER INFORMATION: r= a or g
<221> NAME/KEY: misc_feature
<222> LOCATION: (18)..(18)
<223> OTHER INFORMATION: r= a or g
<221> NAME/KEY: misc_feature
<222> LOCATION: (12)..(12)
<223> OTHER INFORMATION: y= c or t
<221> NAME/KEY: misc_feature
<222> LOCATION: (15)..(15)
<223> OTHER INFORMATION: y= c or t

<400> SEQUENCE: 7
tcnckngcra aytcytcrtc ngt                                         23

<210> SEQ ID NO 8
<211> LENGTH: 22
<212> TYPE: DNA
<213> ORGANISM: primer LOXDG1522U
<220> FEATURE:
<221> NAME/KEY: misc_feature
<222> LOCATION: (1)..(1)
<223> OTHER INFORMATION: w=a or t
<221> NAME/KEY: misc_feature
<222> LOCATION: (2)..(2)
<223> OTHER INFORMATION: s= g or c
<221> NAME/KEY: misc_feature
<222> LOCATION: (3)..(3)
<223> OTHER INFORMATION: n= a or g or c or t
<221> NAME/KEY: misc_feature
<222> LOCATION: (6)..(6)
<223> OTHER INFORMATION: y= c or t
<221> NAME/KEY: misc_feature
<222> LOCATION: (10)..(10)
<223> OTHER INFORMATION: y= c or t
<221> NAME/KEY: misc_feature
<222> LOCATION: (12)..(12)
<223> OTHER INFORMATION: n=a or g or c or t
<221> NAME/KEY: misc_feature
<222> LOCATION: (15)..(15)
<223> OTHER INFORMATION: y=c or t
<221> NAME/KEY: misc_feature
<222> LOCATION: (18)..(18)
<223> OTHER INFORMATION: n= a or g or c or t
<221> NAME/KEY: misc_feature
<222> LOCATION: (21)..(21)
```

<223> OTHER INFORMATION: y=c or t

<400> SEQUENCE: 8
wsncaytggy tnaayacnca yg                                           22

<210> SEQ ID NO 9
<211> LENGTH: 22
<212> TYPE: DNA
<213> ORGANISM: primer LOXDG1552L
<220> FEATURE:
<221> NAME/KEY: misc_feature
<222> LOCATION: (2)..(2)
<223> OTHER INFORMATION: n=a or g or c or t
<221> NAME/KEY: misc_feature
<222> LOCATION: (5)..(5)
<223> OTHER INFORMATION: r= a or g
<221> NAME/KEY: misc_feature
<222> LOCATION: (8)..(8)
<223> OTHER INFORMATION: n=a or g or c or t
<221> NAME/KEY: misc_feature
<222> LOCATION: (11)..(11)
<223> OTHER INFORMATION: r=a or g
<221> NAME/KEY: misc_feature
<222> LOCATION: (14)..(14)
<223> OTHER INFORMATION: n= a or g or c or t
<221> NAME/KEY: misc_feature
<222> LOCATION: (16)..(16)
<223> OTHER INFORMATION: r=a or g
<221> NAME/KEY: misc_feature
<222> LOCATION: (20)..(20)
<223> OTHER INFORMATION: r=a or g

<400> SEQUENCE: 9
cngcrtgngt rttnarccar tg                                           22

<210> SEQ ID NO 10
<211> LENGTH: 23
<212> TYPE: DNA
<213> ORGANISM: primer LOXDG2128L
<220> FEATURE:
<221> NAME/KEY: misc_feature
<222> LOCATION: (3)..(3)
<223> OTHER INFORMATION: n= a or g or c or t
<221> NAME/KEY: misc_feature
<222> LOCATION: (6)..(6)
<223> OTHER INFORMATION: r= a or g
<221> NAME/KEY: misc_feature
<222> LOCATION: (9)..(9)
<223> OTHER INFORMATION: r= a or g
<221> NAME/KEY: misc_feature
<222> LOCATION: (12)..(12)
<223> OTHER INFORMATION: n= a or g or c or t
<221> NAME/KEY: misc_feature
<222> LOCATION: (15)..(15)
<223> OTHER INFORMATION: n= a or g or c or t
<221> NAME/KEY: misc_feature
<222> LOCATION: (18)..(18)
<223> OTHER INFORMATION: n= a or g or c or t
<221> NAME/KEY: misc_feature
<222> LOCATION: (21)..(21)
<223> OTHER INFORMATION: r=a or g

<400> SEQUENCE: 10
tgnccraart tnacngcngc rtg                                          23

<210> SEQ ID NO 11
<211> LENGTH: 639
<212> TYPE: DNA
<213> ORGANISM: primer
<220> FEATURE:
<221> NAME/KEY: misc_feature
<223> OTHER INFORMATION: LOX genomic Clone 10 forward sequencing primer
<221> NAME/KEY: misc_feature
<222> LOCATION: (482)..(482)
<223> OTHER INFORMATION: r= a or g
<221> NAME/KEY: misc_feature
<222> LOCATION: (554)..(554)
<223> OTHER INFORMATION: r= a or g

<400> SEQUENCE: 11

```
tacgactcac tagggcga attgggccct ctagatgcat gctcgagcgg ccgccagtgt     60
gatggatatc tgcagaattc ggcttacgga tgaggagttt gcgcgggaaa tgctggctgg    120
actcaaccca gttgtcatcc gactactcca agtaaactac agcttccttt caaataattt    180
ttaatgccct gtttgttttc tgagaaaatg aacttggaa aggcttccag actttgtttt    240
ctttccctcc atctactgtt ctagctcttt tctgataatt attgtctttc tattttgttt    300
gaaggagttt cctccaaaaa gcaagctgga tcctgaagtt tatggcaacc aaaacagttc    360
aataaccaaa gaacacatag agaatcacct ggatgacctt actataaacg aggtaacgct    420
cttaggttcc cttctttcaa actaaatttt tcaatgtcga catgttaatt ttttgcattg    480
gracacaagc catagtaact gaaaaatggt gcgttttact aaggcaatgg agaagaagag    540
gctattcata ttaratcacc atgatgtttt catgccatac ctgaggagga taaacacaac    600
ttccacgaaa acatacgcct caaggactct cctcttcct                          639
```

<210> SEQ ID NO 12
<211> LENGTH: 636
<212> TYPE: DNA
<213> ORGANISM: primer
<220> FEATURE:
<221> NAME/KEY: misc_feature
<223> OTHER INFORMATION: LOX genomic Clone 10 reverse sequencing primer

<400> SEQUENCE: 12

```
tcaagcttgg taccgagctc ggatccacta gtaacggccg ccagtgtgct ggaattcggc     60
tttggccgaa attgacggcg gcgtggagag cagaagccac ccagatgata atggtgcatg    120
tttctatcag ctcttgaca gtacgcattt taggccacca aggctcgtcc ttcttgtcgc    180
catgaccctc ttccctgact ccttccacc aggactgaag ctcagagtct ttctggacca    240
tctcatctgt cttgtagtag aatgagcaat actctttcac ccatgtctca atagctgacc    300
agatctcaag tccatcaaca gcatagggt agtcatctat cagtaggcgg agtccatgag    360
gggcctctga atcctcaacc gccattcctc tgaaagagtg cccaagttgg agcatatcag    420
ttagatgaaa atcacaattt tcactagatt cattgcacag caggaaagaa acaatcact    480
aacagtattt atatacctct tgatgagatc agcaggaagt gcttgctcag tgagaaccca    540
gtctttgtaa acaacagatg acatttccat ggcatacttt gatggaaaaa ctgtgctctc    600
caccactcca ccagcattga tgaggatttg tcgagc                             636
```

<210> SEQ ID NO 13
<211> LENGTH: 23
<212> TYPE: DNA
<213> ORGANISM: primer LOX1 ExtL

<400> SEQUENCE: 13

```
ttcaggatcc agcttgcttt ttg                                            23
```

<210> SEQ ID NO 14
<211> LENGTH: 23
<212> TYPE: DNA
<213> ORGANISM: primer LOX2 IntL -continued

```
<400> SEQUENCE: 14
tgaggcgtat gttttcgtgg aag                                    23

<210> SEQ ID NO 15
<211> LENGTH: 23
<212> TYPE: DNA
<213> ORGANISM: primer LOX2 ExtU

<400> SEQUENCE: 15
acacaacttc cacgaaaaca tac                                    23

<210> SEQ ID NO 16
<211> LENGTH: 23
<212> TYPE: DNA
<213> ORGANISM: primer LOX3 IntU

<400> SEQUENCE: 16
atcctcatca atgctggtgg agt                                    23

<210> SEQ ID NO 17
<211> LENGTH: 23
<212> TYPE: DNA
<213> ORGANISM: LOX1 IntU

<400> SEQUENCE: 17
caaaaagcaa gctggatcct gaa                                    23

<210> SEQ ID NO 18
<211> LENGTH: 20
<212> TYPE: DNA
<213> ORGANISM: LOX3 ExtL

<400> SEQUENCE: 18
aaactgtgct ctccaccact                                        20

<210> SEQ ID NO 19
<211> LENGTH: 23
<212> TYPE: DNA
<213> ORGANISM: LOX4 ExtU

<400> SEQUENCE: 19
gtcatggcga caagaaggac gag                                    23

<210> SEQ ID NO 20
<211> LENGTH: 20
<212> TYPE: DNA
<213> ORGANISM: LOX4 IntL

<400> SEQUENCE: 20
tcgtccttct tgtcgccatg                                        20

<210> SEQ ID NO 21
<211> LENGTH: 23
<212> TYPE: DNA
<213> ORGANISM: primer LOX 69IntU

<400> SEQUENCE: 21
gatgttttca tgccatacct gag                                    23

<210> SEQ ID NO 22
<211> LENGTH: 19
<212> TYPE: DNA
<213> ORGANISM: primer LOX 1307IntL
```

```
<400> SEQUENCE: 22
ttgccagtaa gcccacctt                                                   19

<210> SEQ ID NO 23
<211> LENGTH: 1196
<212> TYPE: DNA
<213> ORGANISM: Vitis vinifera cv. Cabernet Sauvignon stem cDNA library

<400> SEQUENCE: 23
tggcatgaaa catcaaacta cgcctcaagg actctcctct tcctgaaaga cgacggaact        60
ttgaagccgc tggcgattga attgagccta ccacatccta atggggataa attcggagct       120
gtcaacaaag tatacacacc agctgaagat ggcgttgaag gttccatttg gcagctggct       180
aaagcttatg ctgctgtgaa tgactctggc tatcatcagc tcctcagcca ctggttgaat       240
acacatgctg caattgagcc atttgtgatt gcaaccaaca ggcagctcag tgtgcttcac       300
ccaattcaca gcttttgca tcctcacttc cgtgatacga tgaatataaa tgcattagct       360
cgacaaatcc tcatcaatgc tggtggagtg gtggagagca cagttttcc atcaaagtat       420 gccatggaaa tgtcatctgt tgtttacaaa gactgggttc tcactgagca agcacttcct       480
gctgatctca tcaagagagg aatggcggtt gaggattcag aggcccctca tggactccgc       540
ctactgatag atgactaccc ctatgctgtg atggacttga atctggtca gctattgaga       600 catgggtgaa agagtattgc tcattctacc acaagacaga tgagatggtc cagaaagact       660
ctgagcttca gttctggtgg aaggaagtca gggaagaggg tcatggcgac aagaaggacg       720
agccttggtg gcctaaaatg cgtactgtca aagagctgat acaaacatgc accattatca       780
tctgggtggc ttctgctctc catgctgcag tgaatttcgg gcagtaccct tatgcaggct       840 acctccccaaa ccgcccaacg ataagccgca gattcatgcc tgaagaaggc actcctgagt       900
atgaagaact caagtccaat cctgataagg ctttcctgaa acaatcact gcccagctgc       960 agaccttct tggcatctcc cttattgagg tcctttccag gcattcttcc gatgaggttt      1020
atcttggaca gagagacact cctgaatgga ccctggacgc aacaccattg aaagcttttg      1080
agaaattcgg aaggaagctg gcagacattg aagagaggat catagataga aatggaaatg      1140
agagattcaa gaacagagtt gggcctgtga agataccata cactgttatg atgcca         1196

<210> SEQ ID NO 24
<211> LENGTH: 19
<212> TYPE: DNA
<213> ORGANISM: primer LOX 1018U

<400> SEQUENCE: 24
ctacctccca aaccgccca                                                   19

<210> SEQ ID NO 25
<211> LENGTH: 19
<212> TYPE: DNA
<213> ORGANISM: primer LOX 1036L

<400> SEQUENCE: 25
tgggcggttt gggaggtag                                                   19

<210> SEQ ID NO 26
<211> LENGTH: 22
<212> TYPE: DNA
<213> ORGANISM: primer LOX1146U
```

```
<400> SEQUENCE: 26
ttcttggcat ctcccttatt ga                                              22

<210> SEQ ID NO 27
<211> LENGTH: 22
<212> TYPE: DNA
<213> ORGANISM: primer LOX 1167L

<400> SEQUENCE: 27
tcaataaggg agatgccaag aa                                              22

<210> SEQ ID NO 28
<211> LENGTH: 21
<212> TYPE: DNA
<213> ORGANISM: primer LOX 117L

<400> SEQUENCE: 28
tgaccttgaa tgcagactcg c                                               21

<210> SEQ ID NO 29
<211> LENGTH: 23
<212> TYPE: DNA
<213> ORGANISM: primer 123U

<400> SEQUENCE: 29
gactgggatg aggagattgg aga                                             23

<210> SEQ ID NO 30
<211> LENGTH: 20
<212> TYPE: DNA
<213> ORGANISM: primer LOX 1361U

<400> SEQUENCE: 30
acactgctct accccacaag                                                 20

<210> SEQ ID NO 31
<211> LENGTH: 20
<212> TYPE: DNA
<213> ORGANISM: primer LOX 1380L

<400> SEQUENCE: 31
cttgtggggt agagcagtgt                                                 20

<210> SEQ ID NO 32
<211> LENGTH: 23
<212> TYPE: DNA
<213> ORGANISM: primer LOX 145L

<400> SEQUENCE: 32
tctccaatct cctcatccca gtc                                             23

<210> SEQ ID NO 33
<211> LENGTH: 20
<212> TYPE: DNA
<213> ORGANISM: primer LOX 1697U

<400> SEQUENCE: 33
catggtgatc ctggtgagtt                                                 20

<210> SEQ ID NO 34
<211> LENGTH: 22
<212> TYPE: DNA
<213> ORGANISM: primer LOX 27U
```

```
<400> SEQUENCE: 34
ttacagggga aaattggaaa ac                                              22

<210> SEQ ID NO 35
<211> LENGTH: 27
<212> TYPE: DNA
<213> ORGANISM: primer LOX 2953L

<400> SEQUENCE: 35
ccaagtatgc tggttttcca attttcc                                         27

<210> SEQ ID NO 36
<211> LENGTH: 27
<212> TYPE: DNA
<213> ORGANISM: primer LOX 3020L

<400> SEQUENCE: 36
cagtcgaacg tgaccttgaa tgcagac                                         27

<210> SEQ ID NO 37
<211> LENGTH: 27
<212> TYPE: DNA
<213> ORGANISM: primer LOX 3406L

<400> SEQUENCE: 37
ctgtacttgc gcagtggccc tggtgtt                                         27

<210> SEQ ID NO 38
<211> LENGTH: 27
<212> TYPE: DNA
<213> ORGANISM: primer LOX 3461L

<400> SEQUENCE: 38
ccattcctta agctctccgg ttccatc                                         27

<210> SEQ ID NO 39
<211> LENGTH: 22
<212> TYPE: DNA
<213> ORGANISM: primer LOX 48L

<400> SEQUENCE: 39
gttttccaat tttccctgt aa                                               22

<210> SEQ ID NO 40
<211> LENGTH: 21
<212> TYPE: DNA
<213> ORGANISM: primer  LOX 625U

<400> SEQUENCE: 40
atatgattga tttctgctct t                                               21

<210> SEQ ID NO 41
<211> LENGTH: 23
<212> TYPE: DNA
<213> ORGANISM: primer LOX 6588U

<400> SEQUENCE: 41
gtccatttga agaagtgtga gac                                             23

<210> SEQ ID NO 42
<211> LENGTH: 23
<212> TYPE: DNA
```

-continued

```
<213> ORGANISM: primer LOX 69L

<400> SEQUENCE: 42
ctcaggtatg gcatgaaaac atc                                              23

<210> SEQ ID NO 43
<211> LENGTH: 21
<212> TYPE: DNA
<213> ORGANISM: primer LOX940L

<400> SEQUENCE: 43
agcattgatg aggatttgtc g                                                21

<210> SEQ ID NO 44
<211> LENGTH: 20
<212> TYPE: DNA
<213> ORGANISM: primer LOX 950L

<400> SEQUENCE: 44
ccactccacc agcattgatg                                                  20

<210> SEQ ID NO 45
<211> LENGTH: 21
<212> TYPE: DNA
<213> ORGANISM: primer LOX 97U

<400> SEQUENCE: 45
gcgagtctgc attcaaggtc a                                                21
```